United States Patent
Scheland

(10) Patent No.: US 10,912,654 B2
(45) Date of Patent: Feb. 9, 2021

(54) METHOD AND APPARATUS FOR FUSING A JOINT

(71) Applicant: Apical Healthcare Solutions Inc., Durham, PA (US)

(72) Inventor: John A. Scheland, Old Forge, PA (US)

(73) Assignee: Apical Healthcare Solutions Inc., Durham, PA (US)

( * ) Notice: Subject to any disclaimer, the term of this patent is extended or adjusted under 35 U.S.C. 154(b) by 0 days.

(21) Appl. No.: 15/840,264

(22) Filed: Dec. 13, 2017

(65) Prior Publication Data

US 2018/0161174 A1 Jun. 14, 2018

Related U.S. Application Data

(60) Provisional application No. 62/433,342, filed on Dec. 13, 2016.

(51) Int. Cl.
| | |
|---|---|
| A61F 2/46 | (2006.01) |
| A61B 17/86 | (2006.01) |
| A61B 17/68 | (2006.01) |
| A61F 2/30 | (2006.01) |
| A61B 17/56 | (2006.01) |

(52) U.S. Cl.
CPC ............ *A61F 2/4606* (2013.01); *A61B 17/68* (2013.01); *A61B 17/864* (2013.01); *A61B 2017/564* (2013.01); *A61F 2002/30224* (2013.01); *A61F 2002/30507* (2013.01); *A61F 2002/30622* (2013.01)

(58) Field of Classification Search
None
See application file for complete search history.

(56) References Cited

U.S. PATENT DOCUMENTS

| | | | |
|---|---|---|---|
| 7,172,627 B2 | 2/2007 | Fiere et al. | |
| 7,594,931 B2 | 9/2009 | Louis et al. | |
| 8,784,498 B2 | 7/2014 | Scheland | |
| 2002/0147499 A1* | 10/2002 | Shea | A61B 17/80 623/22.21 |
| 2003/0153919 A1* | 8/2003 | Harris | A61B 17/8057 606/291 |
| 2004/0176852 A1 | 9/2004 | Zubok et al. | |

(Continued)

*Primary Examiner* — Leslie Lopez
(74) *Attorney, Agent, or Firm* — Pandiscio & Pandiscio

(57) ABSTRACT

Apparatus for stabilizing a first portion of bone relative to a second portion of bone, the apparatus comprising: a fusion barrel for disposition between the first portion of bone and the second portion of bone, the fusion barrel comprising: a generally-cylindrical body having a distal end, a proximal end, and a cavity formed in the generally-cylindrical body, the cavity comprising a distal end and a proximal end; at least one opening formed in the generally-cylindrical body in fluid communication with the cavity of the generally-cylindrical body; and a radially-extending flange extending distally and radially of the distal end of the generally-cylindrical body such that the radially-extending flange extends around at least a portion of the distal end of the generally-cylindrical body; wherein the radially-extending flange comprises a plurality of openings; and a cap configured to be releasably mounted to the proximal end of the generally-cylindrical body so as to substantially seal the proximal end of the cavity.

15 Claims, 25 Drawing Sheets

(56) References Cited

U.S. PATENT DOCUMENTS

| | | | |
|---|---|---|---|
| 2007/0198016 A1 | 8/2007 | Zang et al. | |
| 2010/0280555 A1* | 11/2010 | Aflatoon | A61B 17/3468 606/279 |
| 2016/0242820 A1* | 8/2016 | Whipple | A61B 17/7055 |

* cited by examiner

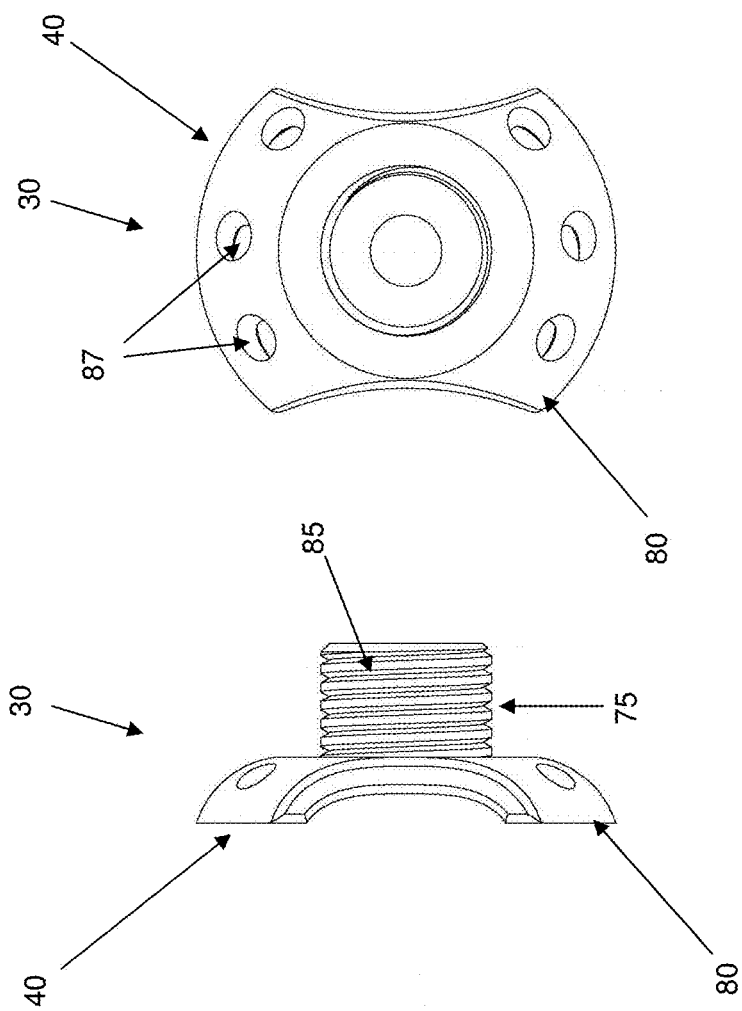
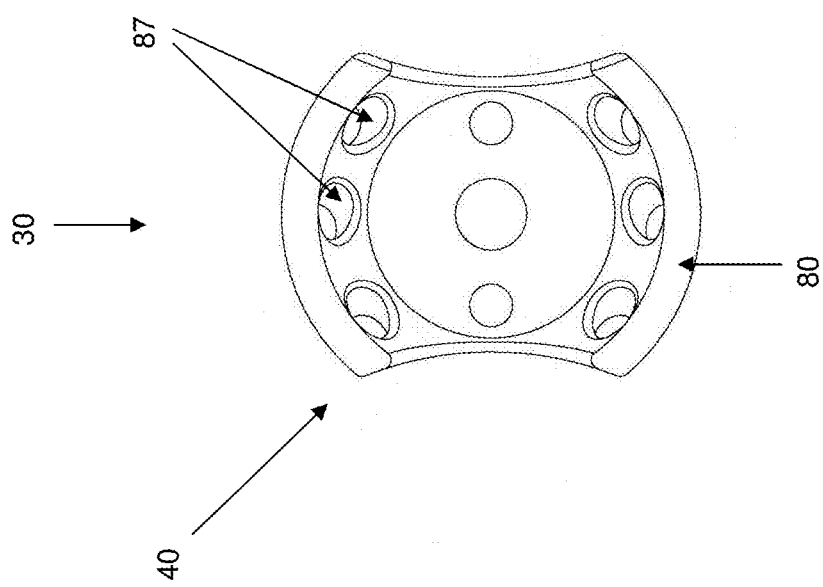
FIG. 5C  FIG. 5B  FIG. 5A

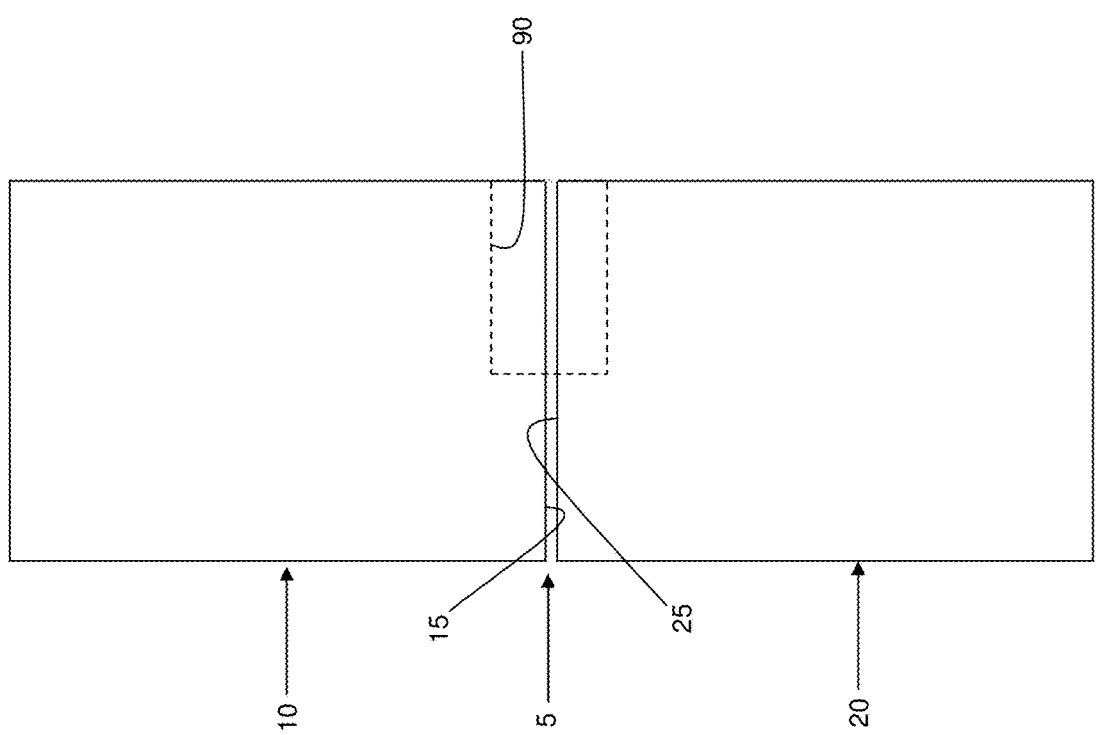

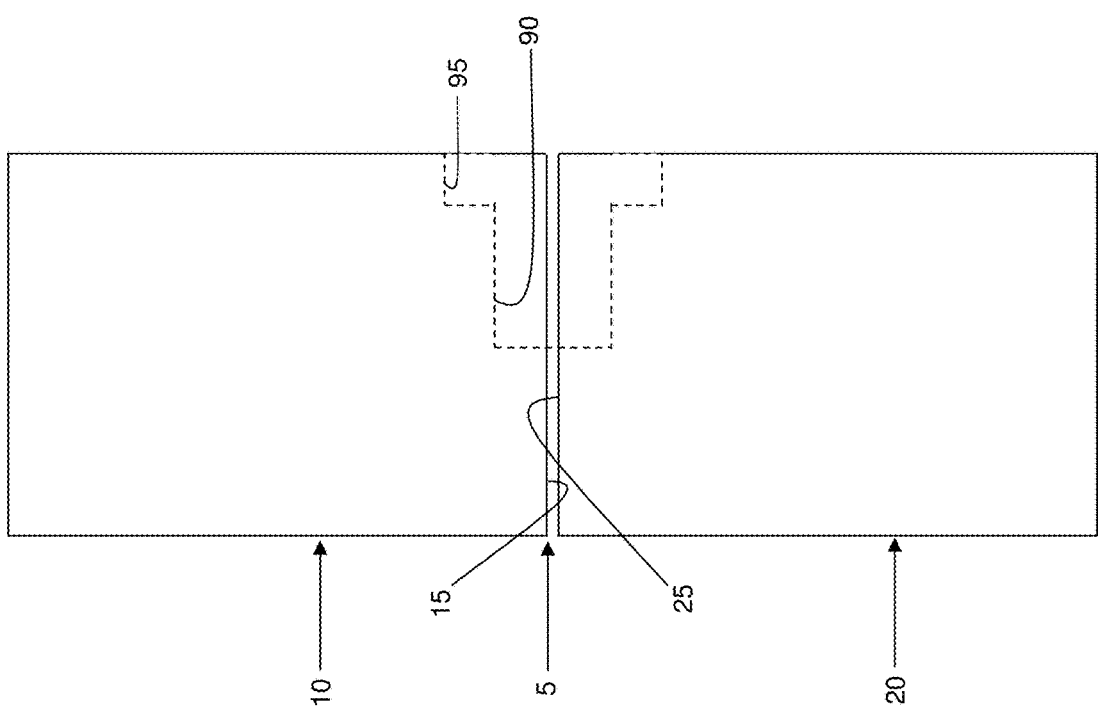

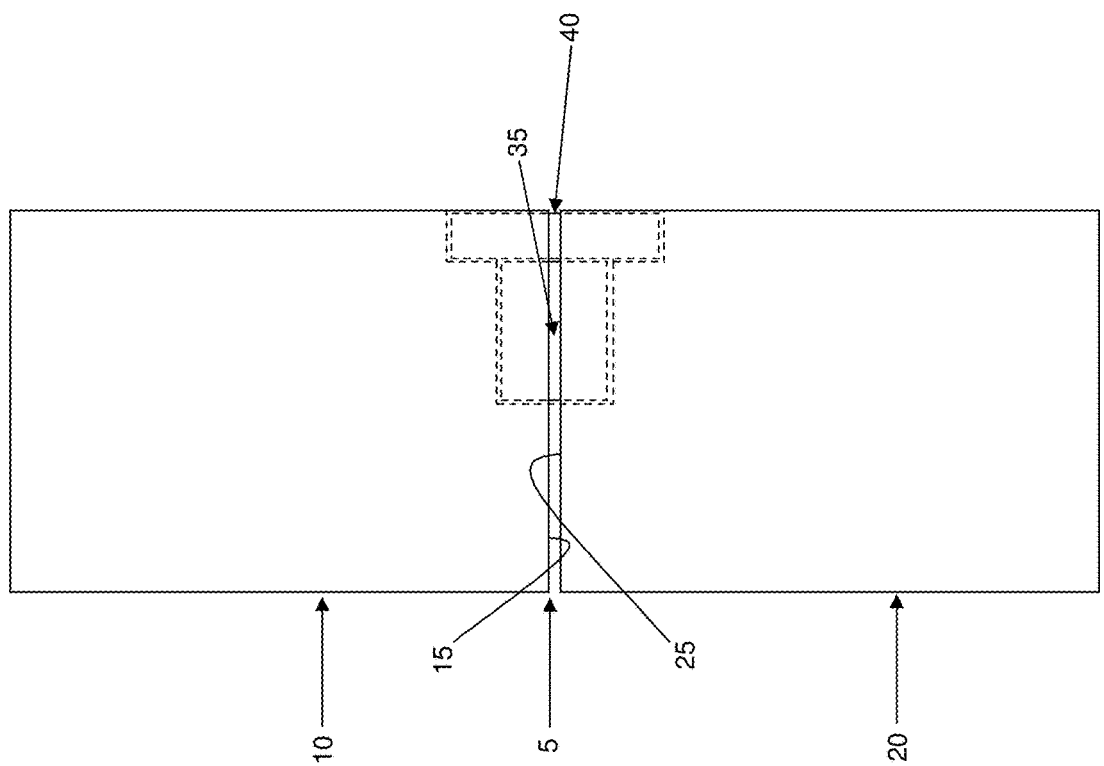

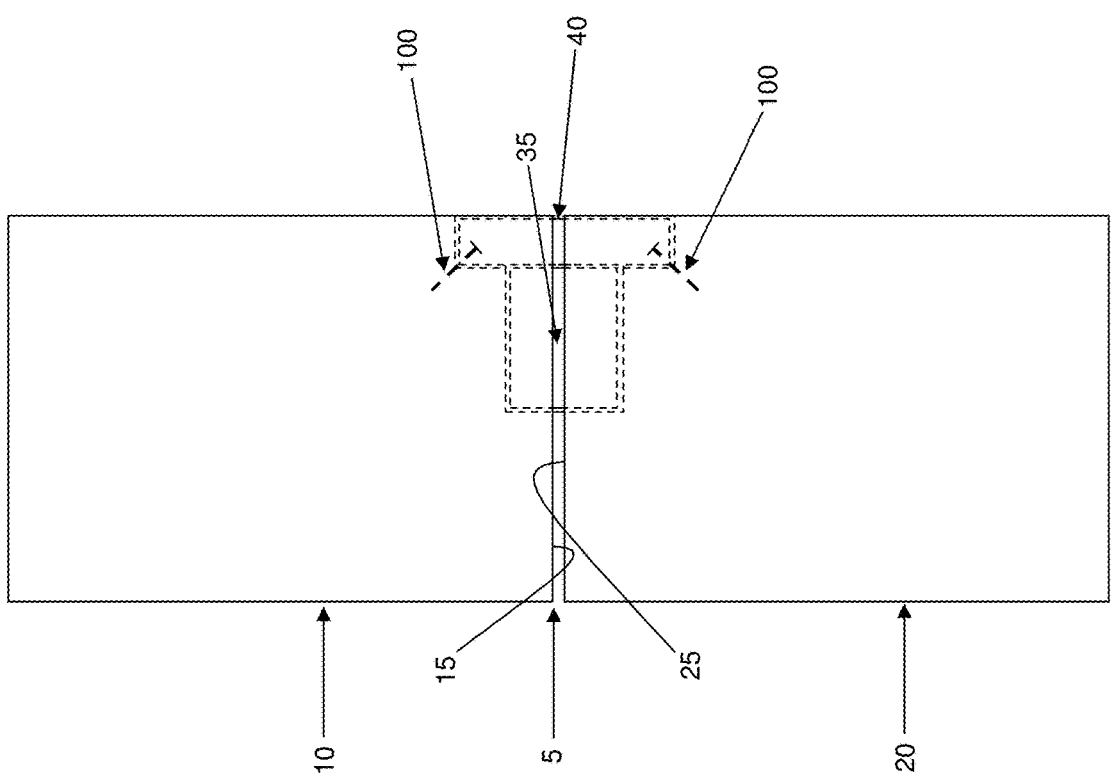

METHOD AND APPARATUS FOR FUSING A JOINT

REFERENCE TO PENDING PRIOR PATENT APPLICATION

This patent application claims benefit of pending prior U.S. Provisional Patent Application Ser. No. 62/433,342, filed Dec. 13, 2016 for METHOD AND APPARATUS FOR FUSING A JOINT, INCLUDING THE PROVISION AND USE OF A "FUSION BULLET" DEVICE, which patent application is hereby incorporated herein by reference.

FIELD OF THE INVENTION

This invention relates to medical apparatus and procedures in general, and more particularly to medical apparatus and procedures for fusing a joint.

BACKGROUND OF THE INVENTION

A joint can deteriorate for a variety of reasons, e.g., overuse, injury and/or disease. In some situations this deterioration can be substantial, so that the patient experiences significant pain and normal lifestyle is impaired.

Depending on the joint involved and a variety of other factors, the patient suffering from substantial joint deterioration may be a candidate for joint replacement surgery. By way of example but not limitation, total hip arthroplasty (THA) and total knee arthroplasty (TKA) are relatively common procedures which typically yield highly beneficial results.

However, in some circumstances the patient may not be a good candidate for joint replacement surgery. This may be due to the joint involved and/or other factors. By way of example but not limitation, joint replacement surgery is significantly less common for joints such as the ankle, wrist, thumb, toe, finger and vertebrae. In these situations, and others, it may be desirable to perform a joint fusion procedure in order to treat the deteriorated joint.

In a joint fusion procedure, the ends of two bones are fused together so that they unify into a single stable structure. While such a procedure reduces skeletal mobility, since it effectively eliminates the motion of the fused joint, the procedure can nonetheless provide the patient with significant pain relief and improved skeletal stability and strength.

The present invention provides a new and improved method and apparatus for fusing a joint.

SUMMARY OF THE INVENTION

The present invention comprises the provision and use of a new and improved method and apparatus for fusing a joint. More particularly, the present invention comprises a novel "fusion bullet" for disposition within the space between two bones (e.g., in the joint between two articulating bones) that are to be fused together. The novel fusion bullet is preferably configured to be secured to adjacent bone using one or more fasteners. The novel fusion bullet preferably comprises an internal cavity into which bone may grow and/or into which a bone graft material and/or a bone growth promoting material may be disposed (e.g., so as to promote bone in-growth into the implant).

In a preferred form of the present invention, there is provided apparatus for stabilizing a first portion of bone relative to a second portion of bone, said apparatus comprising:

a fusion barrel for disposition between the first portion of bone and the second portion of bone, said fusion barrel comprising:
 a generally-cylindrical body comprising a distal end, a proximal end, and a cavity formed within said generally-cylindrical body; and
 at least one opening formed in said generally-cylindrical body in fluid communication with said cavity of said generally-cylindrical body; and
 a cap configured to be selectively mounted to said proximal end of said body, said cap comprising a radially-extending flange; and
 a plurality of openings formed in said radially-extending flange.

In another preferred form of the present invention, there is provided a method for stabilizing a first portion of bone relative to a second portion of bone, said method comprising:

providing apparatus comprising:
 a fusion barrel for disposition between the first portion of bone and the second portion of bone, said fusion barrel comprising:
  a generally-cylindrical body comprising a distal end, a proximal end, and a cavity formed within said generally-cylindrical body; and
  at least one opening formed in said generally-cylindrical body in fluid communication with said cavity of said generally-cylindrical body; and
 a cap configured to be selectively mounted to said proximal end of said body, said cap comprising a radially-extending flange; and
 a plurality of openings formed in said radially-extending flange;

forming a hole in bone such that that the hole is disposed between the first portion of bone and the second portion of bone;

inserting said generally-cylindrical body of said fusion barrel into the hole;

mounting said cap to said generally-cylindrical body of said fusion barrel; and passing at least one fastener through one of said plurality of openings in said radially-extending flange such that said at least one fastener passes into at least one of the first portion of bone and the second portion of bone.

In another preferred form of the present invention, there is provided apparatus for stabilizing a first portion of bone relative to a second portion of bone, said apparatus comprising:

a fusion barrel for disposition between the first portion of bone and the second portion of bone, said fusion barrel comprising:
 a generally-cylindrical body having a distal end, a proximal end, and a cavity formed in said generally-cylindrical body, said cavity comprising a distal end and a proximal end;
 at least one opening formed in said generally-cylindrical body in fluid communication with said cavity of said generally-cylindrical body; and
 a radially-extending flange extending distally and radially of said distal end of said generally-cylindrical body such that said radially-extending flange extends around at least a portion of said distal end of said generally-cylindrical body;
 wherein said radially-extending flange comprises a plurality of openings; and a cap configured to be releasably mounted to said proximal end of said generally-cylindrical body so as to substantially seal said proximal end of said cavity.

In another preferred form of the present invention, there is provided a method for stabilizing a first portion of bone relative to a second portion of bone, said method comprising:
providing apparatus comprising:
a fusion barrel for disposition between the first portion of bone and the second portion of bone, said fusion barrel comprising:
a generally-cylindrical body having a distal end, a proximal end, and a cavity formed in said generally-cylindrical body, said cavity comprising a distal end and a proximal end;
at least one opening formed in said generally-cylindrical body in fluid communication with said cavity of said generally-cylindrical body; and
a radially-extending flange extending distally and radially of said distal end of said generally-cylindrical body such that said radially-extending flange extends around at least a portion of said distal end of said generally-cylindrical body;
wherein said radially-extending flange comprises a plurality of openings; and
a cap configured to be releasably mounted to said proximal end of said generally-cylindrical body so as to substantially seal said proximal end of said cavity;
forming a hole in bone such that the hole is disposed between the first portion of bone and the second portion of bone;
inserting said generally-cylindrical body of said fusion barrel into the hole;
passing at least one fastener through one of said plurality of openings in said radially-extending flange such that said at least one fastener passes into at least one of the first portion of bone and the second portion of bone; and
mounting said cap to said proximal end of said generally-cylindrical body so as to substantially seal said proximal end of said cavity.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 2, 3A, 3B, 3C, 4, 5A, 5B and 5C are schematic views showing a novel fusion barrel for fusing a joint formed in accordance with the present invention;

FIGS. 6-10 are schematic views showing how the novel fusion barrel of FIGS. 2, 3A, 3B, 3C, 4, 5A, 5B and 5C may be inserted into a joint and fixed to adjacent bone so as to fuse a joint;

DETAILED DESCRIPTION OF THE PREFERRED EMBODIMENTS

Novel "Fusion Bullet"

Figure 1:
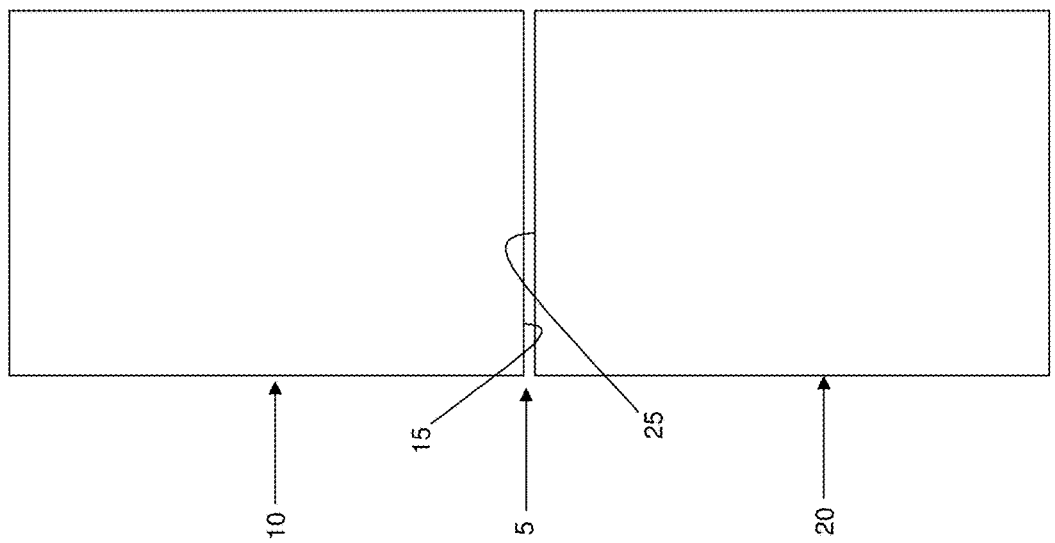
FIG. 1 is a schematic view showing a joint between two adjacent bones.
Figure 2:
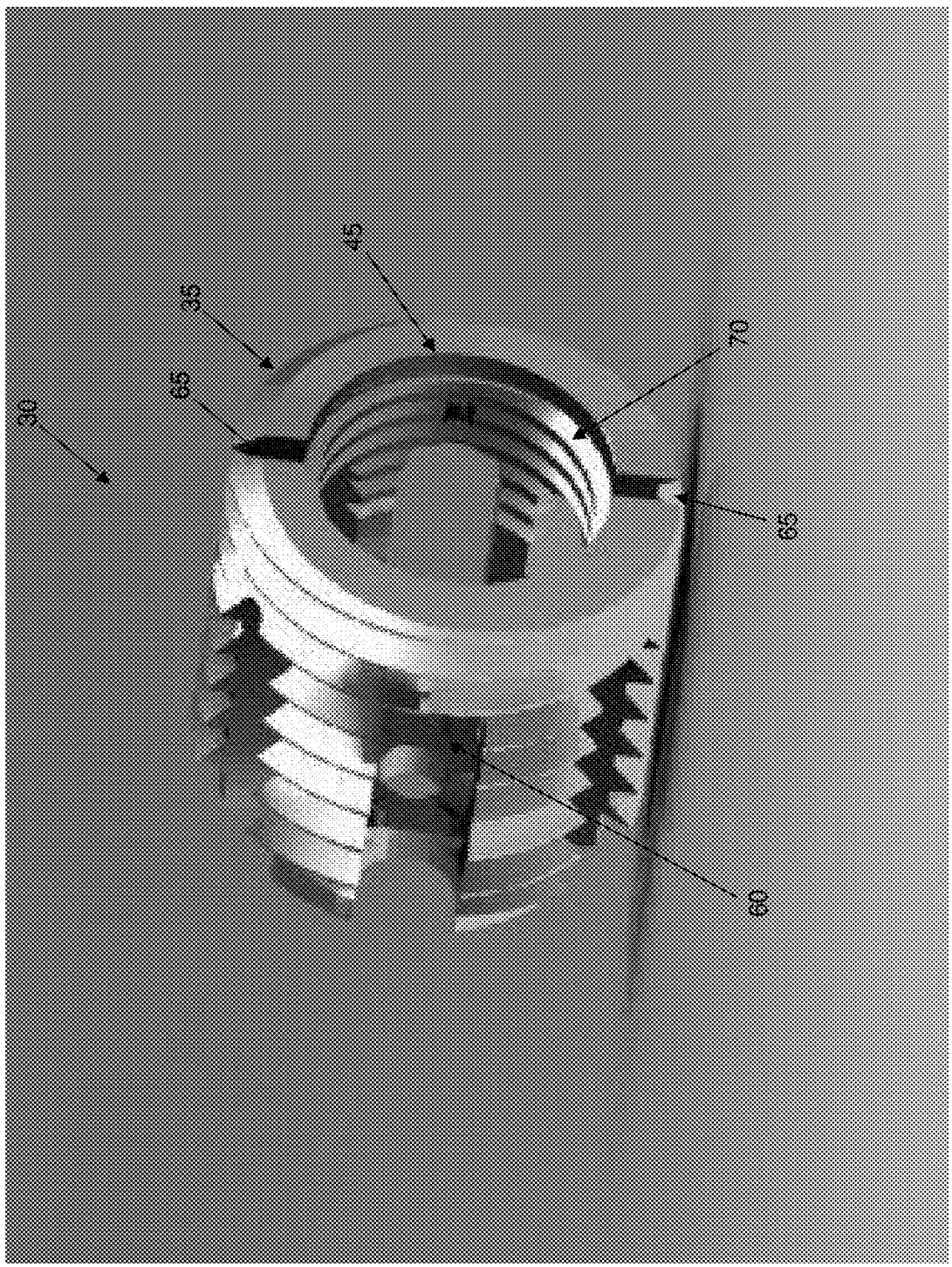
Figure 3C:
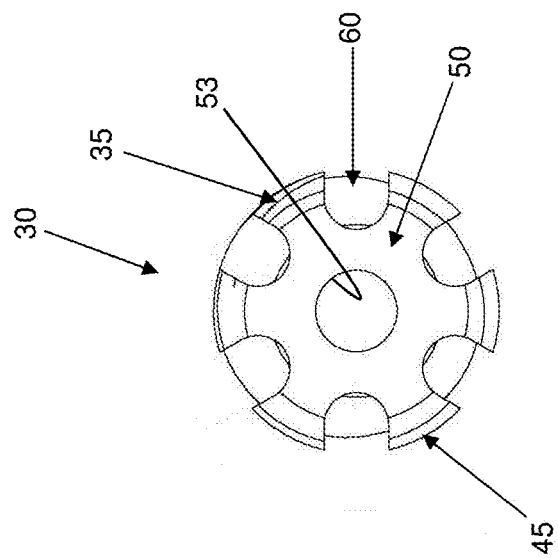
Figure 3B:
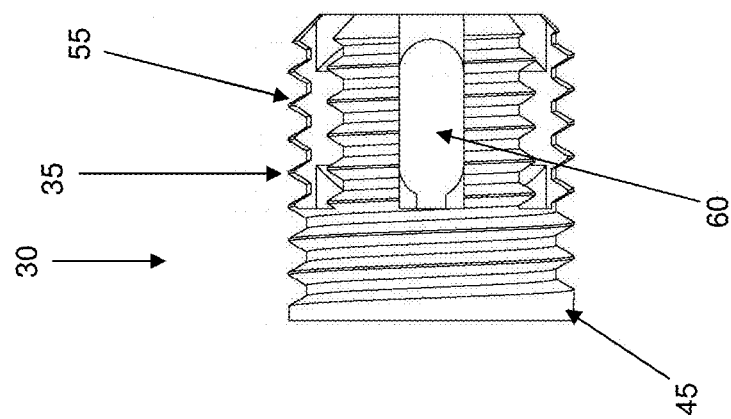
Figure 3A:
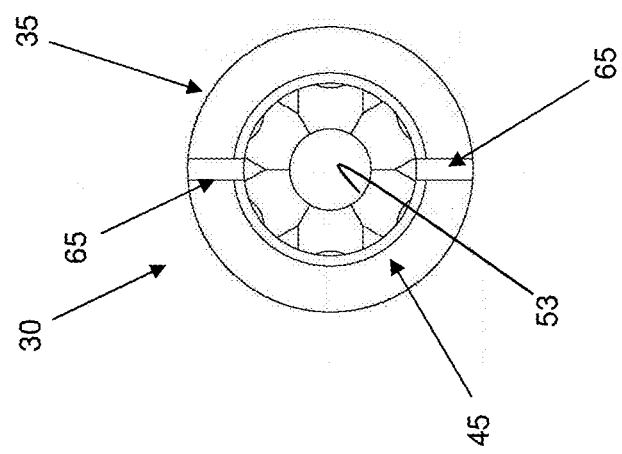
Figure 4:
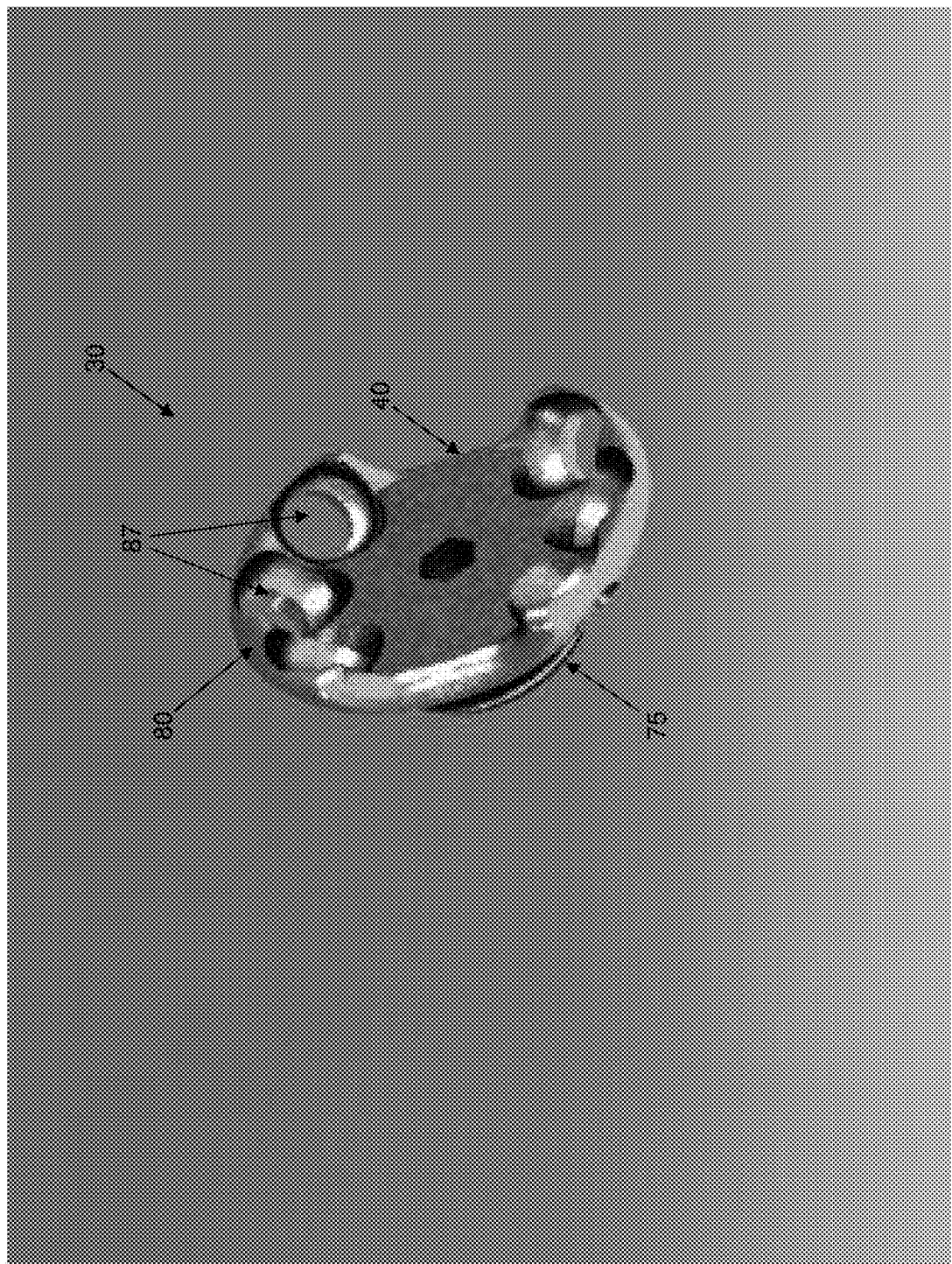

Looking first at FIG. 1, there is shown a simplified schematic representation of an exemplary joint 5. Joint 5 is generally characterized by a first bone 10 having a first articular surface 15 and a second bone 20 having a second articular surface 25.

In accordance with the present invention, and looking now at FIGS. 2, 3A, 3B, 3C, 4, 5A, 5B and 5C, there is provided a novel "fusion bullet" 30 which can be used to fuse a joint. Fusion bullet 30 generally comprises a fusion barrel 35 (FIGS. 2, 3A, 3B and 3C) and a spherical cap 40 (FIGS. 4, 5A, 5B and 5C).

Fusion barrel 35 (FIGS. 2, 3A, 3B and 3C) is characterized by a generally cylindrical, hollow body 45 terminating in a wall 50 at its distal end. If desired, end wall 50 may include one or more openings 53 (e.g., to facilitate bony in-growth into hollow body 45, etc.). In one preferred form of the invention, a first set of screw threads 55 is provided on the outside of fusion barrel 35. This first set of screw threads 55 preferably extends along substantially the entire length of fusion barrel 35. One or more windows 60 (preferably in the form of flutes) are provided on fusion barrel 35, with these windows (flutes) 60 intersecting the first set of screw threads 55 and communicating with the interior of the fusion barrel. A seat 65 (e.g., a pair of diametrically-opposed slots) for receiving a driver (not shown) is preferably provided on the proximal end of fusion barrel 35 (e.g., for receiving the corresponding flat(s) of a driver which may be used to turn fusion barrel 35 and drive fusion bullet 30 into bone). A second set of screw threads 70 is provided on the inside of fusion barrel 35. This second set of screw threads 70 preferably begins at the proximal end of fusion barrel 35 and extends at least part way along the length of the fusion barrel.

A spherical cap 40 is provided to facilitate mounting of fusion barrel 35 to bone, as will hereinafter be discussed in further detail. Spherical cap 40 (FIGS. 4, 5A, 5B and 5C) is characterized by a stem 75 terminating in a substantially spherical head (or flange) 80. Stem 75 includes a set of screw threads 85 extending along the length of stem 75. Screw threads 85 of spherical cap 40 are sized to mate with screw threads 70 of fusion barrel 35 so as to releasably mount spherical cap 40 to fusion barrel 35, as will hereinafter be discussed. Spherical head 80 includes a plurality of openings 87 extending therethrough. Openings 87 may be threaded (i.e., to receive a threaded fastener such as a screw) or openings 87 may be unthreaded.

In use, and looking now at FIG. 6, a bore 90 is drilled across the junction of the first and second articular surfaces 15, 25 so as to remove a hemicylinder of bone material from each bone 10, 20. Bore 90 preferably has a diameter slightly less than the outer diameter of fusion barrel 35. Preferably, bore 90 extends through the hard outer cortical layer of bones 10, 20 and communicates with the soft inner cancellous interiors of bones 10, 20. After bore 90 is formed, a counterbore 95 (FIG. 7) is formed. Counterbore 95 preferably has a diameter substantially the same as the diameter of the substantially spherical head 80 of spherical cap 40.

Figure 8:
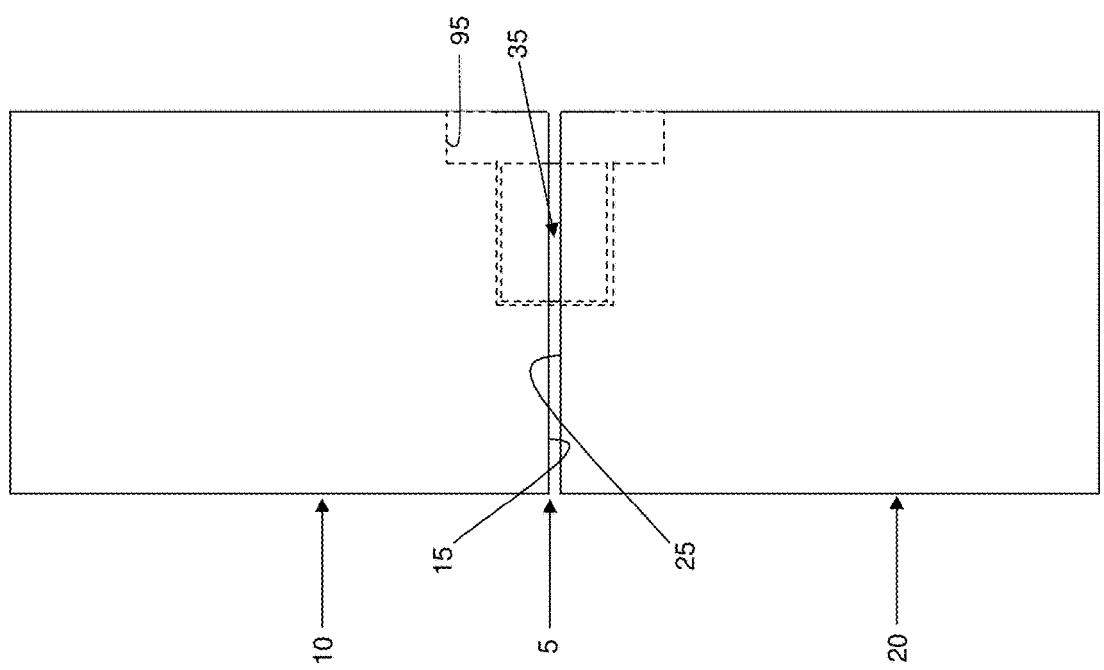
Figure 11D:
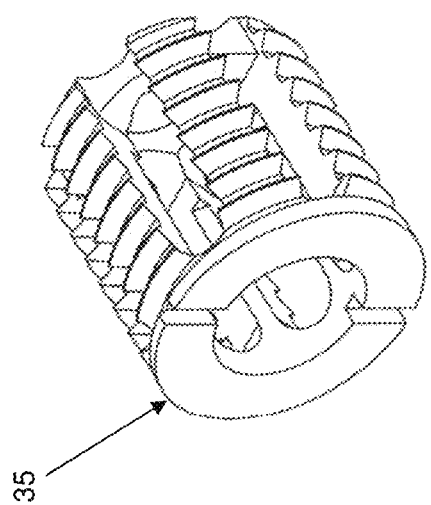
FIGS. 11A, 11B, 11C, 11D and 12-14 are schematic views showing another novel fusion barrel formed in accordance with the present invention.
Figure 11C:
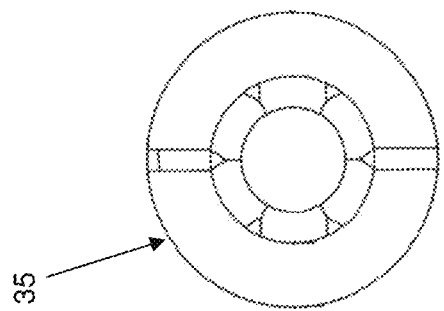
Figure 11B:
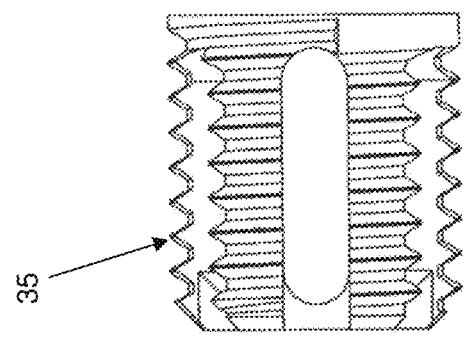
Figure 11A:
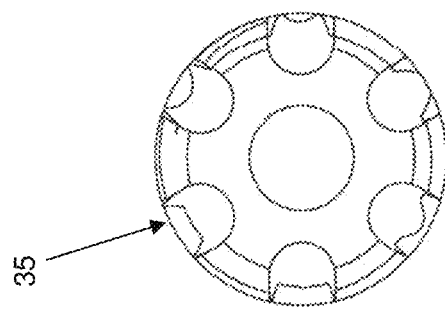
Figure 12:
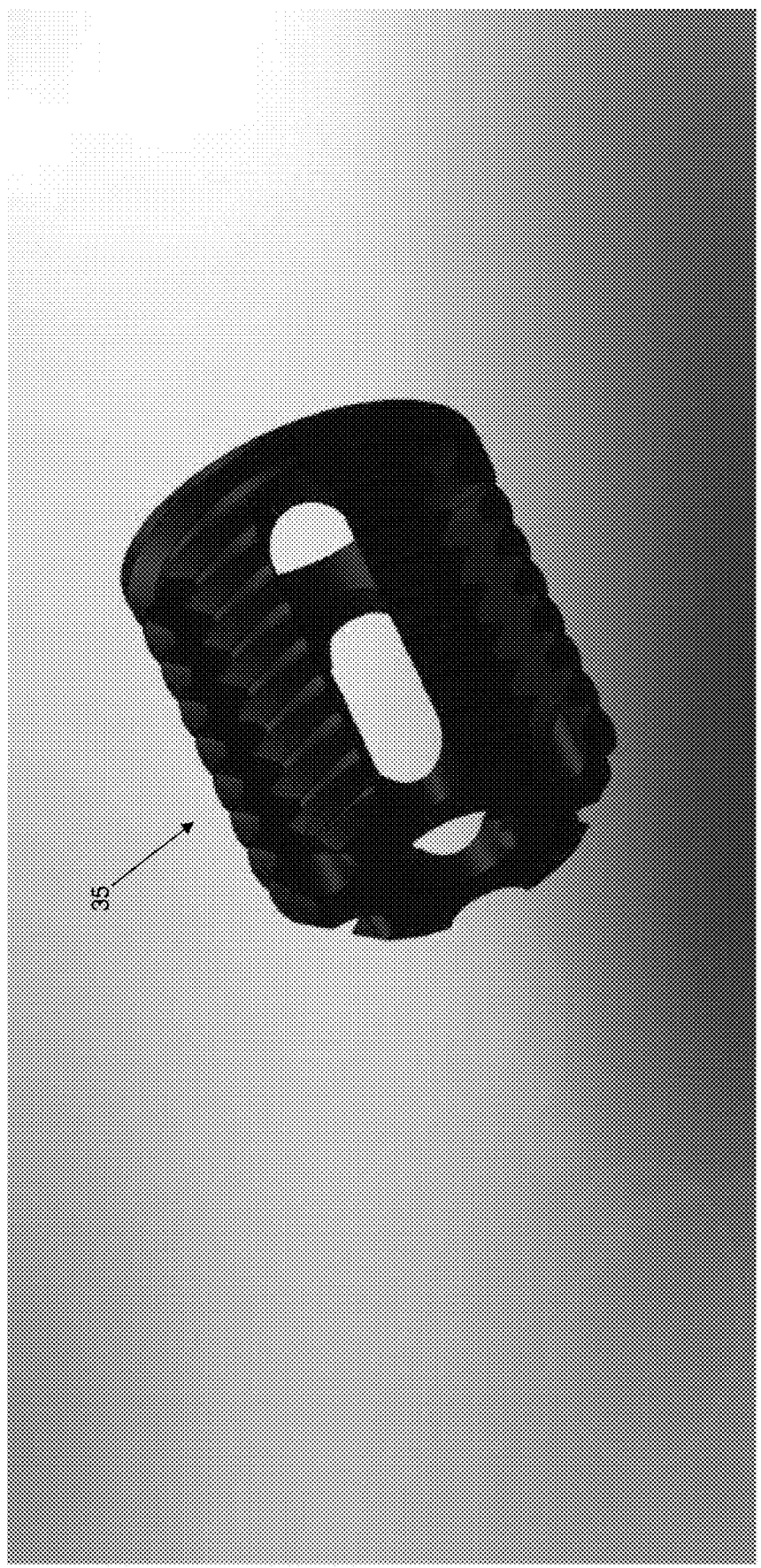
Figure 13:
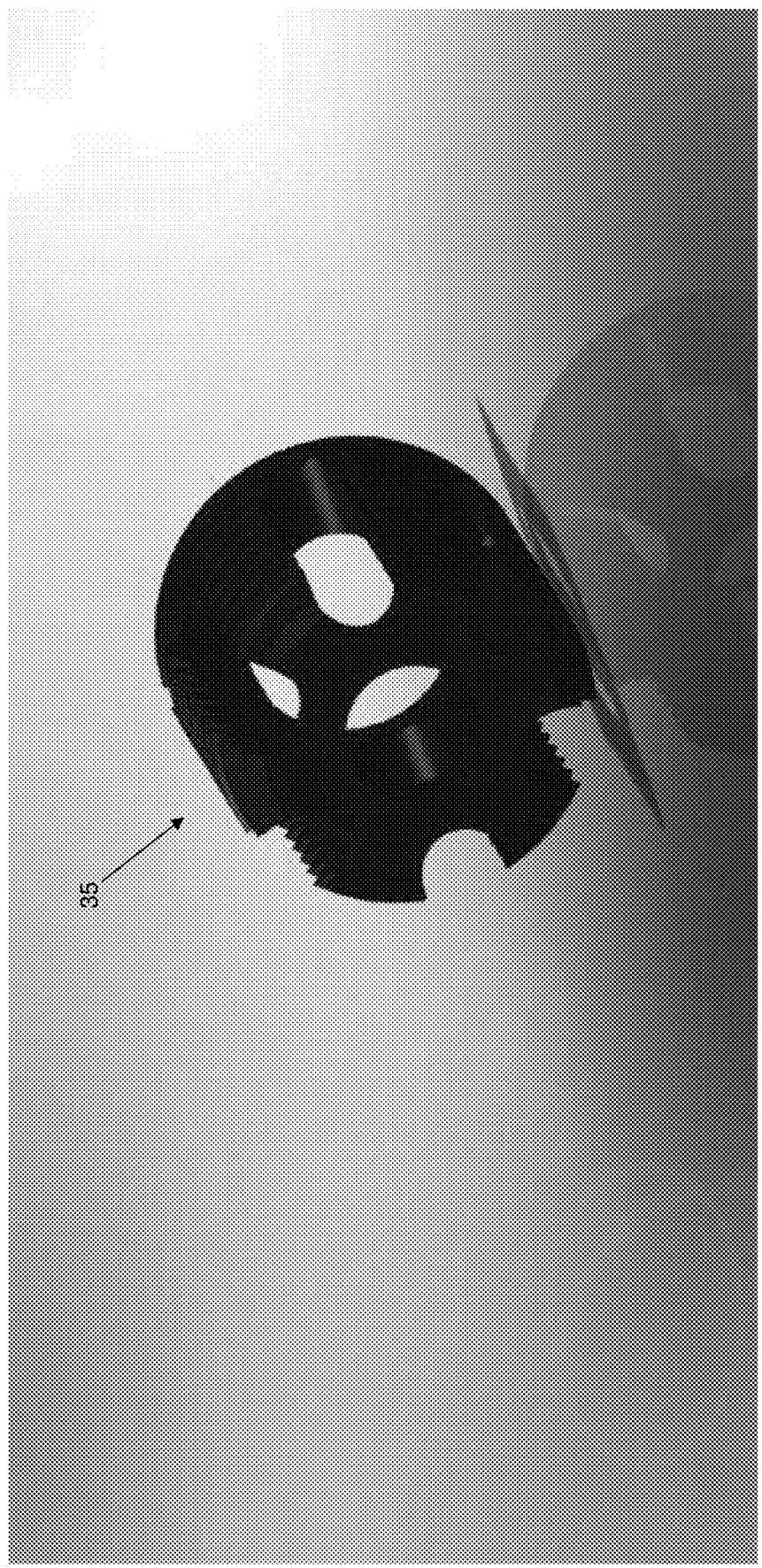
Figure 14:
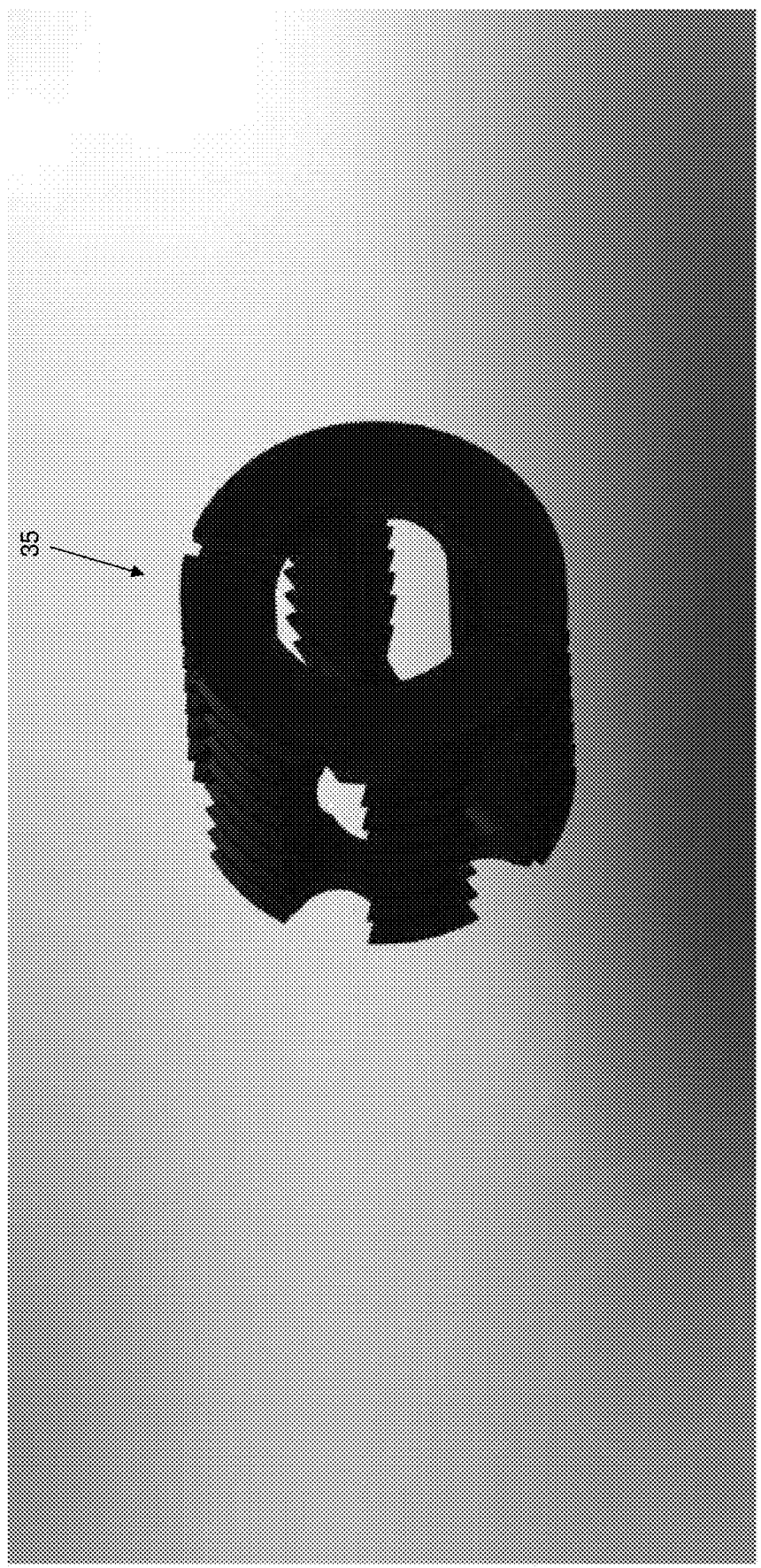
Figure 15:
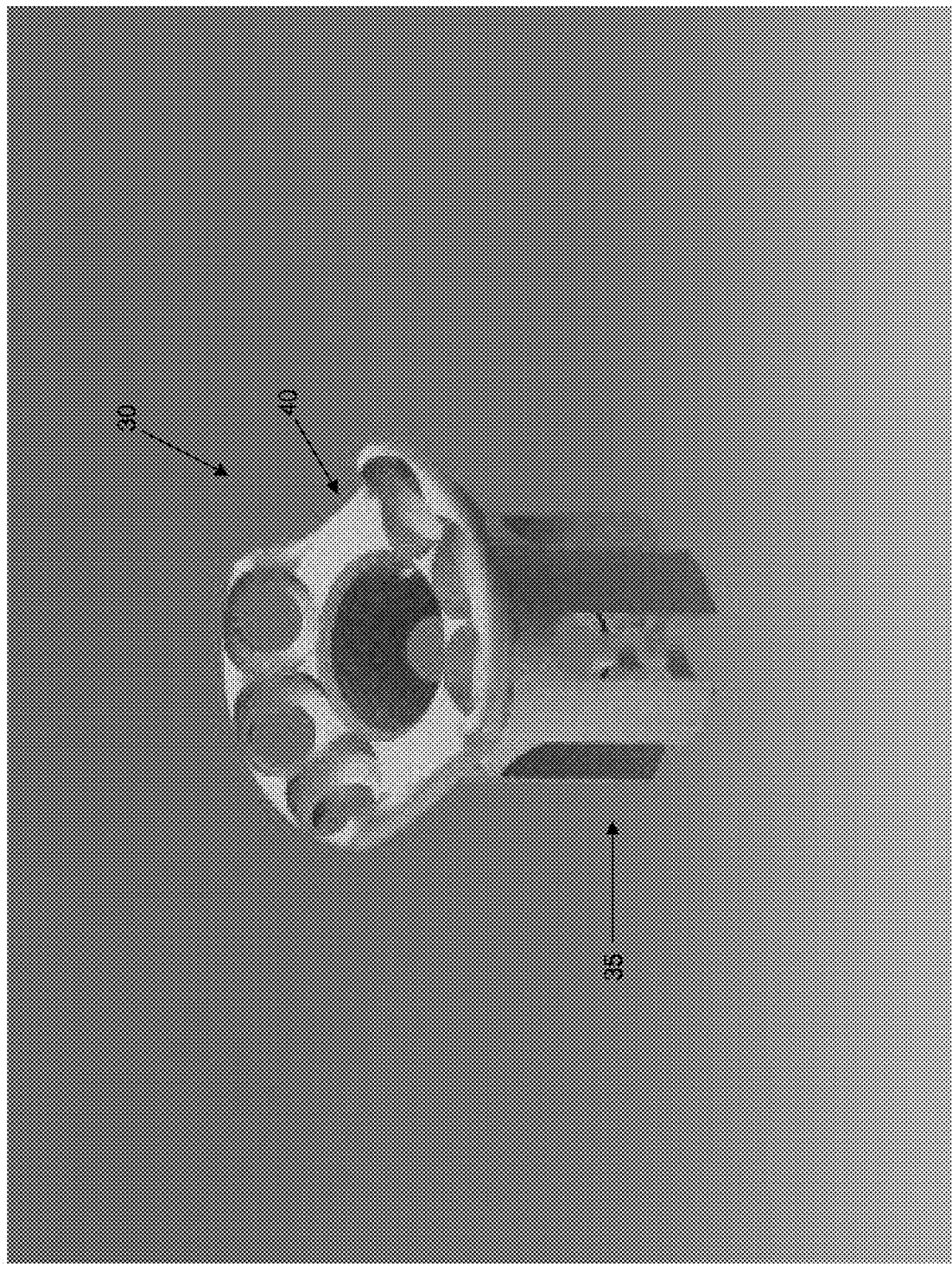
FIGS. 15, 16A, 16B, 16C and 17-19 are schematic views showing still another novel fusion barrel formed in accordance with the present invention.
Figure 16C:
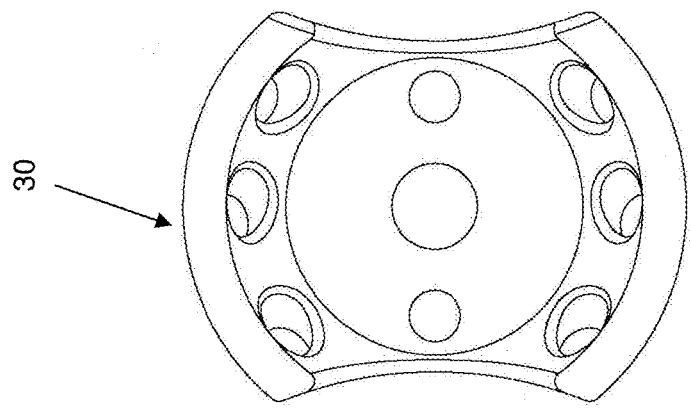
Figure 16B:
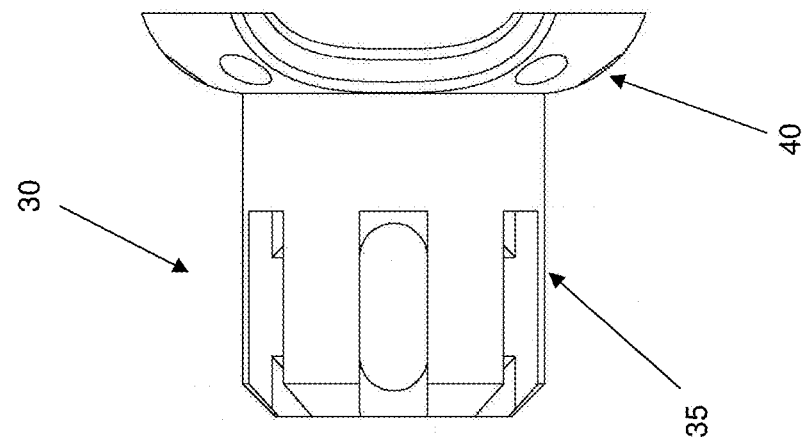
Figure 16A:
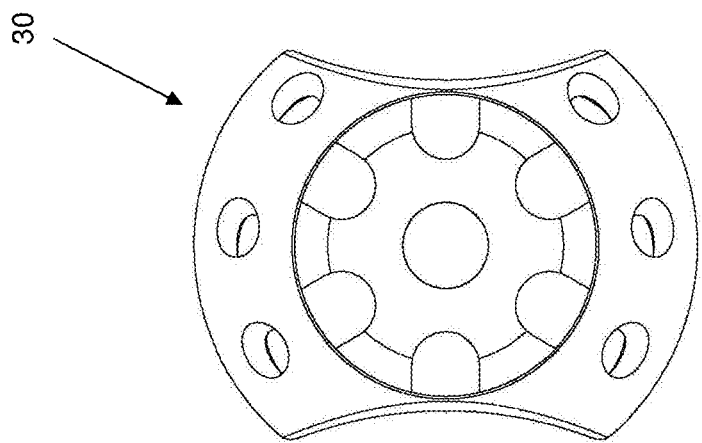

Next, fusion barrel 35 is screwed into bore 90 by turning the fusion barrel with a driver via driver seat 65 formed in the proximal end of the fusion barrel. See FIG. 8. If desired, bone graft material and/or bone growth promoting material may be introduced into the interior of fusion barrel 35, whereby to communicate with the surrounding cancellous bone (e.g., via windows/flutes 60 and wall opening(s) 53), which has been exposed by virtue of drilling bore 90 across the joint line and through the hard outer cortical layers of bones 10, 20 and into the soft cancellous interiors of bones 10, 20.

Next, spherical cap 40 is screwed into fusion barrel 35 by mating stem threads 85 of spherical cap 40 with internal threads 70 of fusion barrel 35 and turning the spherical cap. See FIG. 9. Finally, fasteners (e.g., screws) 100 (FIG. 10) are advanced through openings 87 of spherical head 80 and into the adjacent bone so as to lock fusion bullet 35 into position across the joint line (i.e., across joint 5). By virtue of (i) the engagement of fusion barrel 35 with the surrounding bones 10, 20, and (ii) fasteners (e.g., screws) 100 locking spherical cap 40 to the surrounding bones 10, 20, the first and second bones 10, 20 are locked in position relative to one another. Thereafter the bone graft material and/or bone growth promoting material disposed in fusion barrel 35 (and communicating with the cancellous bone via windows/flutes 60 and wall opening(s) 53) preferably facilitates the growth of new bone across the junction of the two bones 10, 20 (and into fusion barrel 35) so as to fuse the joint.

Second Novel "Fusion Bullet"

FIGS. 11A, 11B, 11C, 11D and 12-14 show another form of fusion bullet 30 formed in accordance with the present invention. This form of fusion bullet 30 is generally similar to the fusion bullet 30 discussed above, however, in this form of the invention, spherical cap 40 is omitted.

Third Novel "Fusion Bullet"

Looking next at FIGS. 15, 16A, 16B and 16C, in another preferred form of the present invention fusion bullet 30 is formed as a single integral structure, with fusion barrel 35 and spherical cap 40 being permanently joined to one another, e.g., with fusion barrel 35 and spherical cap 40 formed integral with one another. In this form of the invention, and as seen in FIGS. 15, 16A, 16B and 16C, it may also be desirable to omit threads 85 from the exterior of fusion barrel 35.

It should be appreciated that fusion bullet 30 may be made out of any material suitable for implantation into the body (e.g., metal, PEEK, PEEK HA, etc.). Where fusion bullet 30 comprises metal or another suitable material, fusion bullet 30 may be configured to be self-tapping so as to facilitate easy installation into bone. Where fusion bullet 30 comprises plastic (e.g., PEEK), the bone hole may be tapped, or screw threads 55 on the outer surface of fusion barrel 35 may be replaced by flexible ribs.

And it should be appreciated that fusion bullet 30 may be provided in various sizes for use in different applications (e.g., for use in the wrist, hand, foot, ankle, etc.) without departing from the scope of the present invention.

Fourth Novel "Fusion Bullet"

As discussed above, fusion bullet 30 is intended to be inserted into a bone hole, filled with the desired bone graft material, sealed by mounting spherical cap 40 to hollow body 45, and then spherical cap 40 secured to the surrounding bone by passing one or more fasteners (e.g., screws) 100 through holes 87 of spherical head 80 of spherical cap 40 and into the adjacent bone. Thus, with this form of the invention, spherical cap 40 serves the dual functions of (i) sealing the bone graft material within hollow body 45 of fusion body 35, and (ii) providing additional anchoring of fusion bullet 30 to the bone.

However, it has been recognized that it in some circumstances, it may be desirable to insert the fusion bullet into a bone hole, provide additional anchoring of the fusion bullet to the bone using one or more fasteners (e.g., screws) 100, fill the fusion barrel with the desired bone graft material and/or bone growth promoting material, and thereafter seal the fusion barrel with a cap in order to seal the bone graft material within the fusion bullet.

To this end, and looking now at FIGS. 17-23, there is provided a novel fusion bullet 130 which can be used to fuse a joint. Fusion bullet 130 generally comprises a hollow fusion barrel 135 and a removable solid cap 140 (FIG. 18) which may be used to seal the hollow interior of fusion barrel 135, e.g., after bone graft material and/or bone growth promoting material has been disposed in the hollow interior of fusion barrel 135, as will hereinafter be discussed in further detail.

Figure 17:
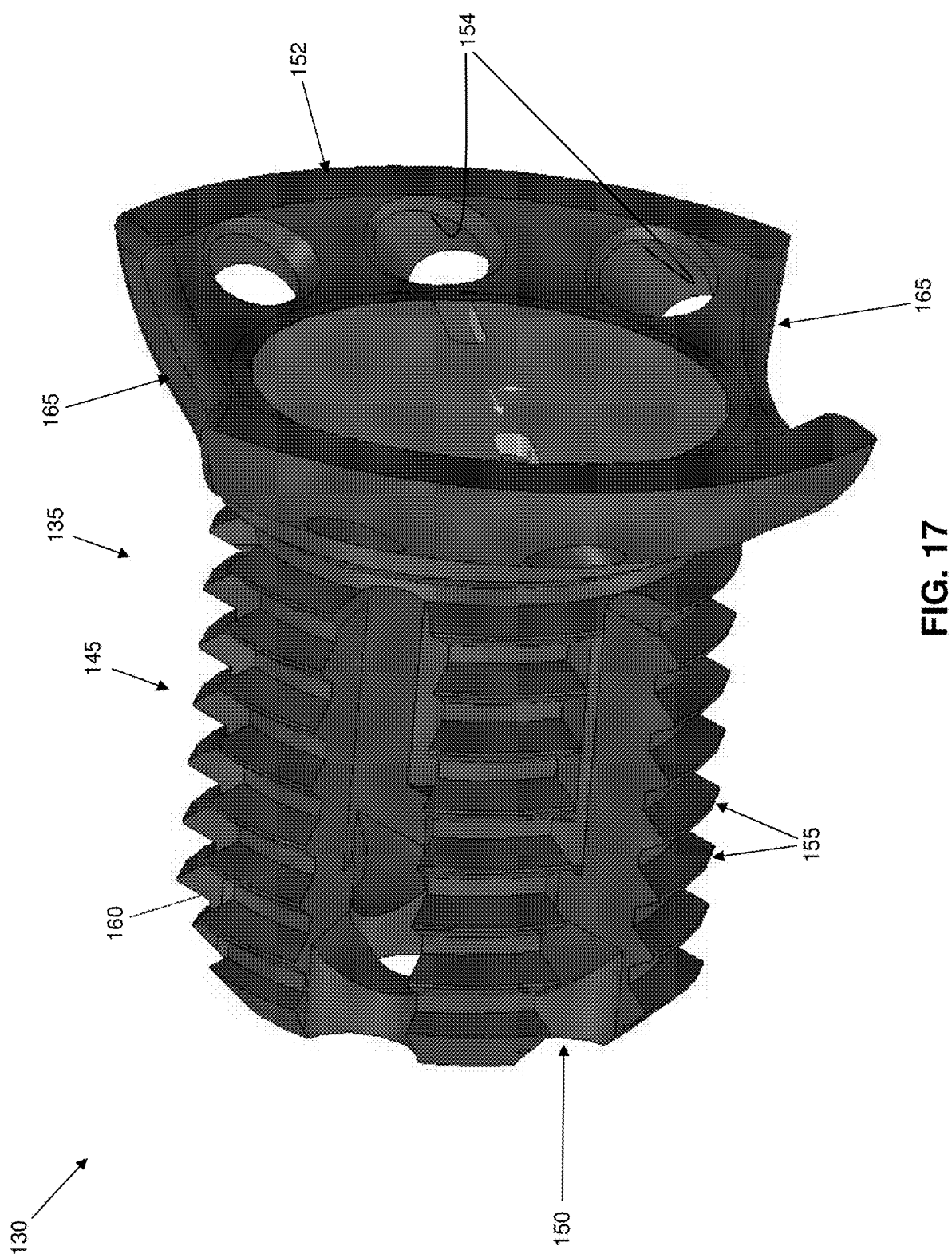
Figure 18:
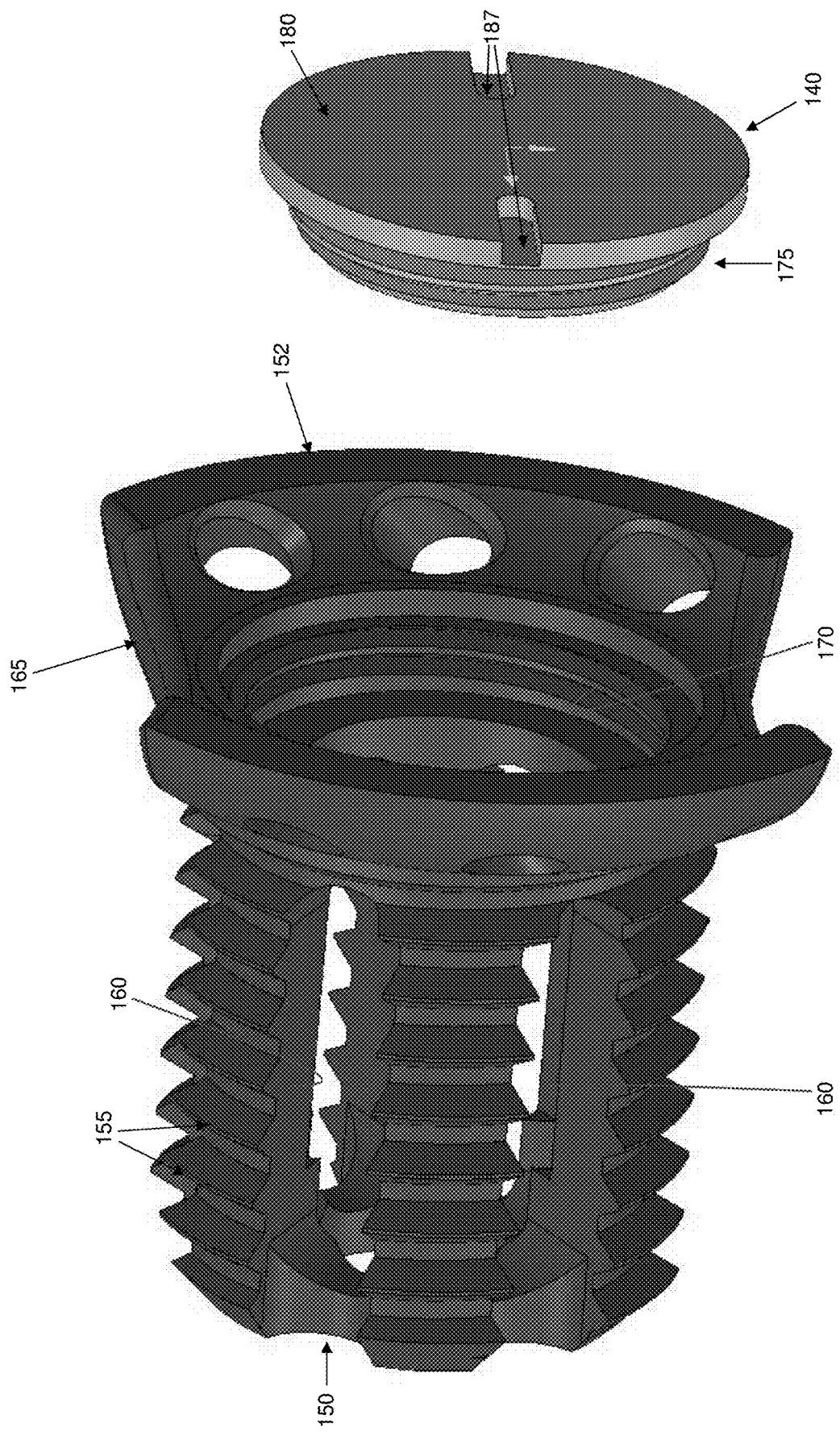
Figure 19:
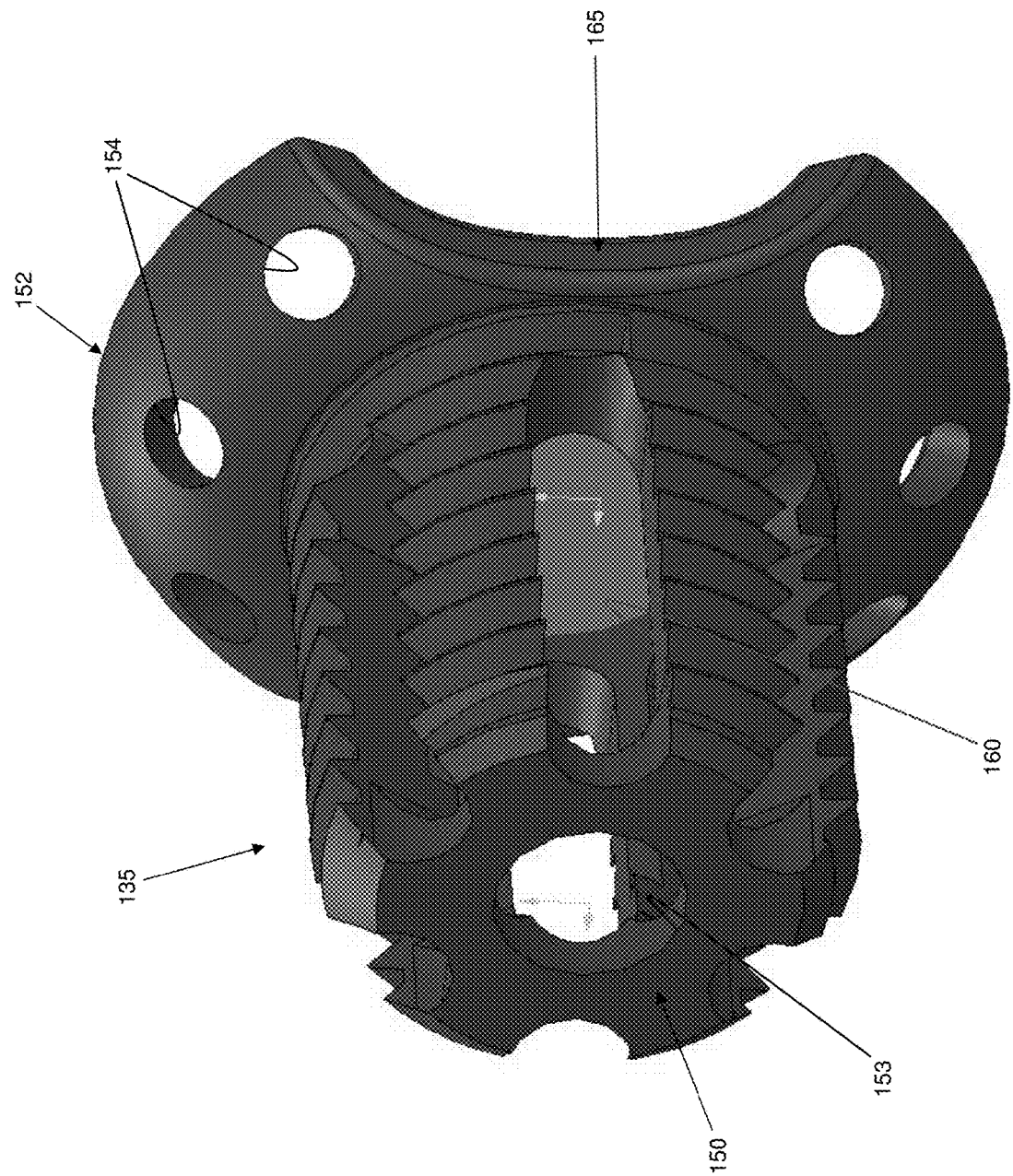
Figure 20:
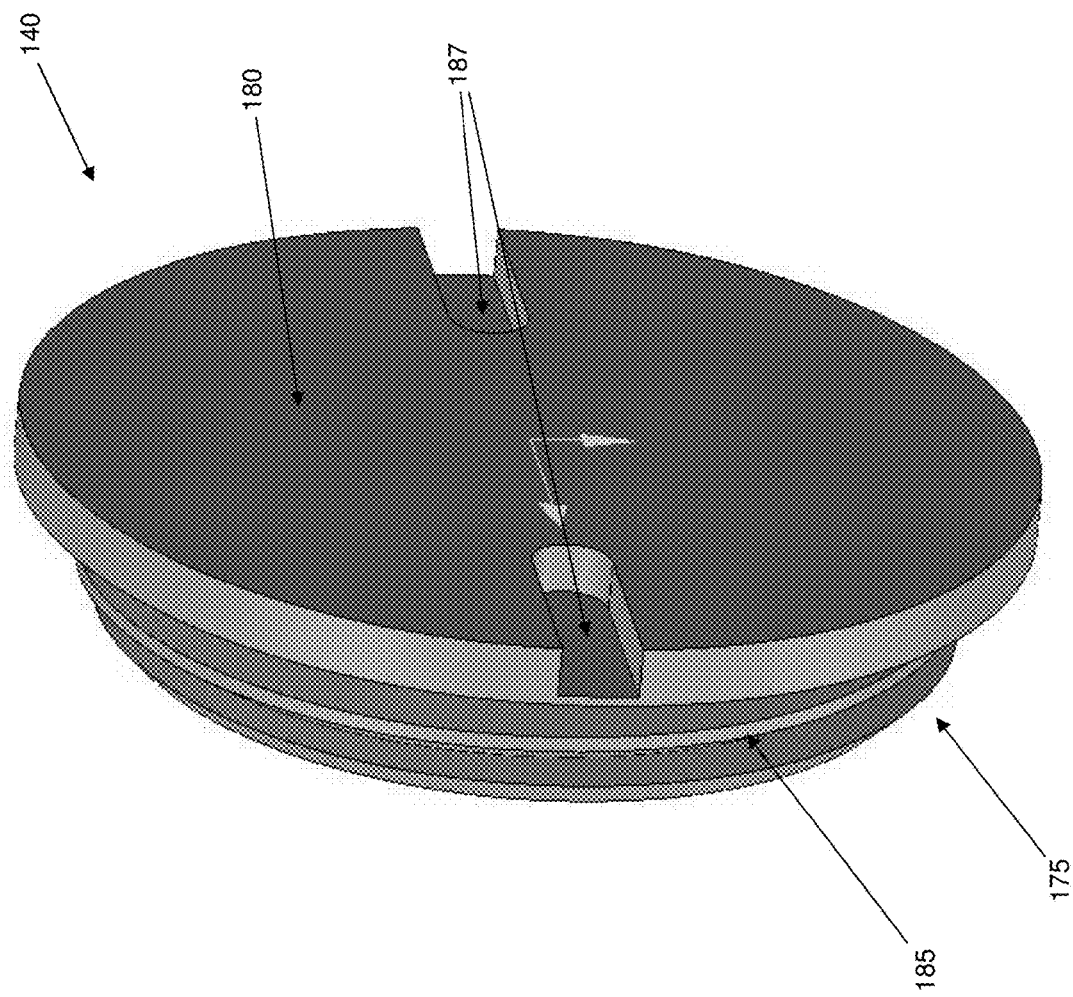
FIGS. 20 and 21 are schematic views showing a novel cap which may be mounted to the novel fusion barrel of FIGS. 15, 16A, 16B, 16C and 17-19.
Figure 21:
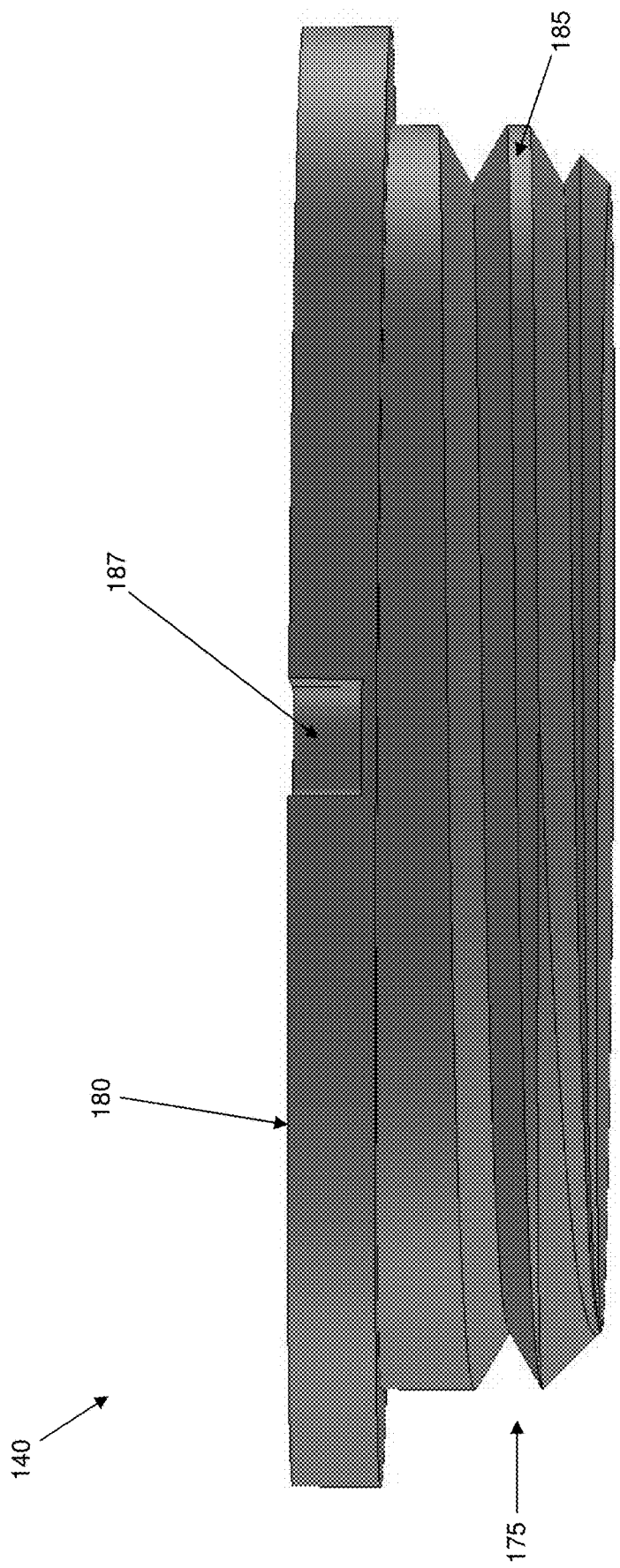
Figure 22:
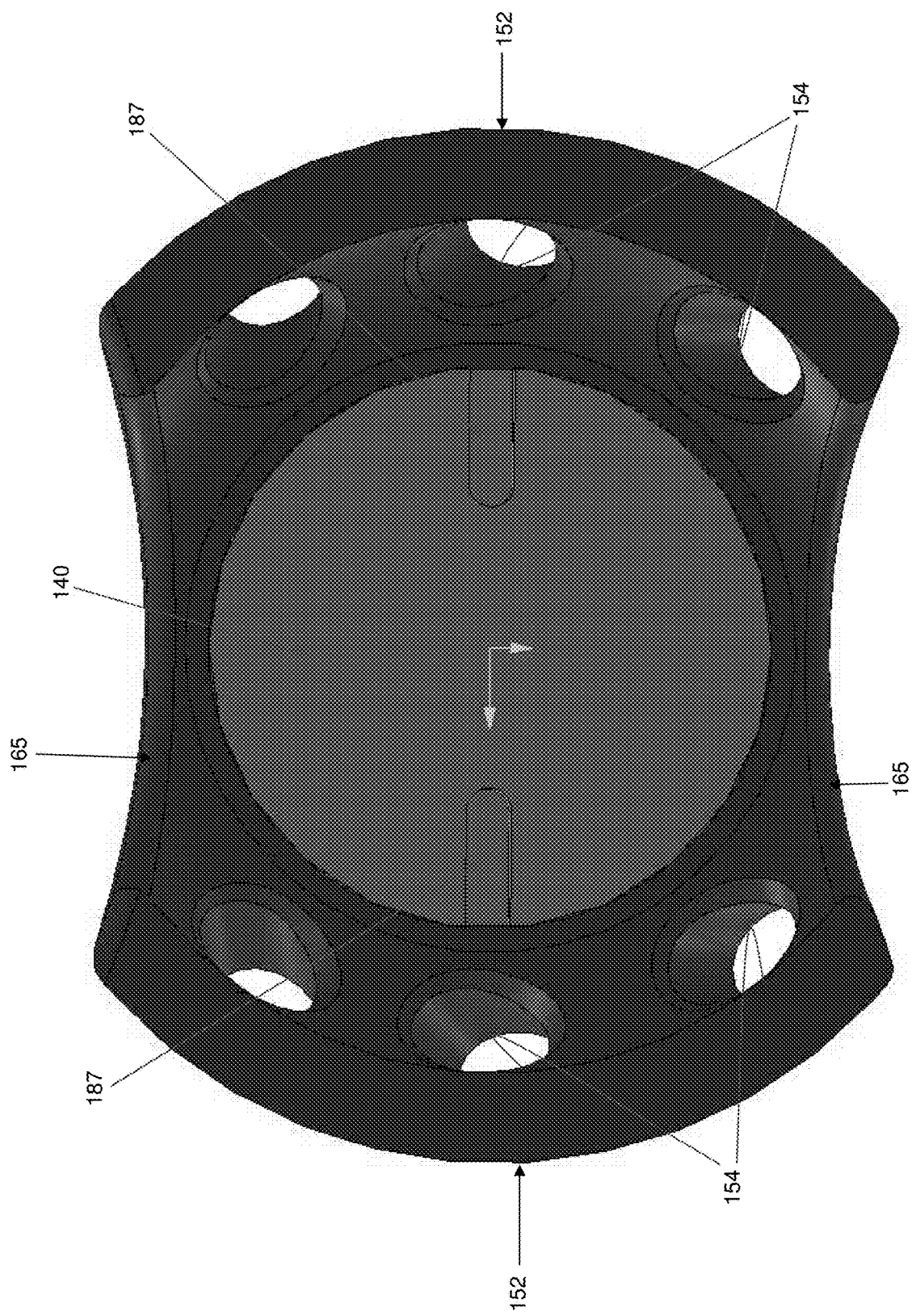
FIGS. 22 and 23 are schematic views showing further aspects of the novel fusion barrel of FIGS. 15, 16A, 16B, 16C and 17-19.
Figure 23:
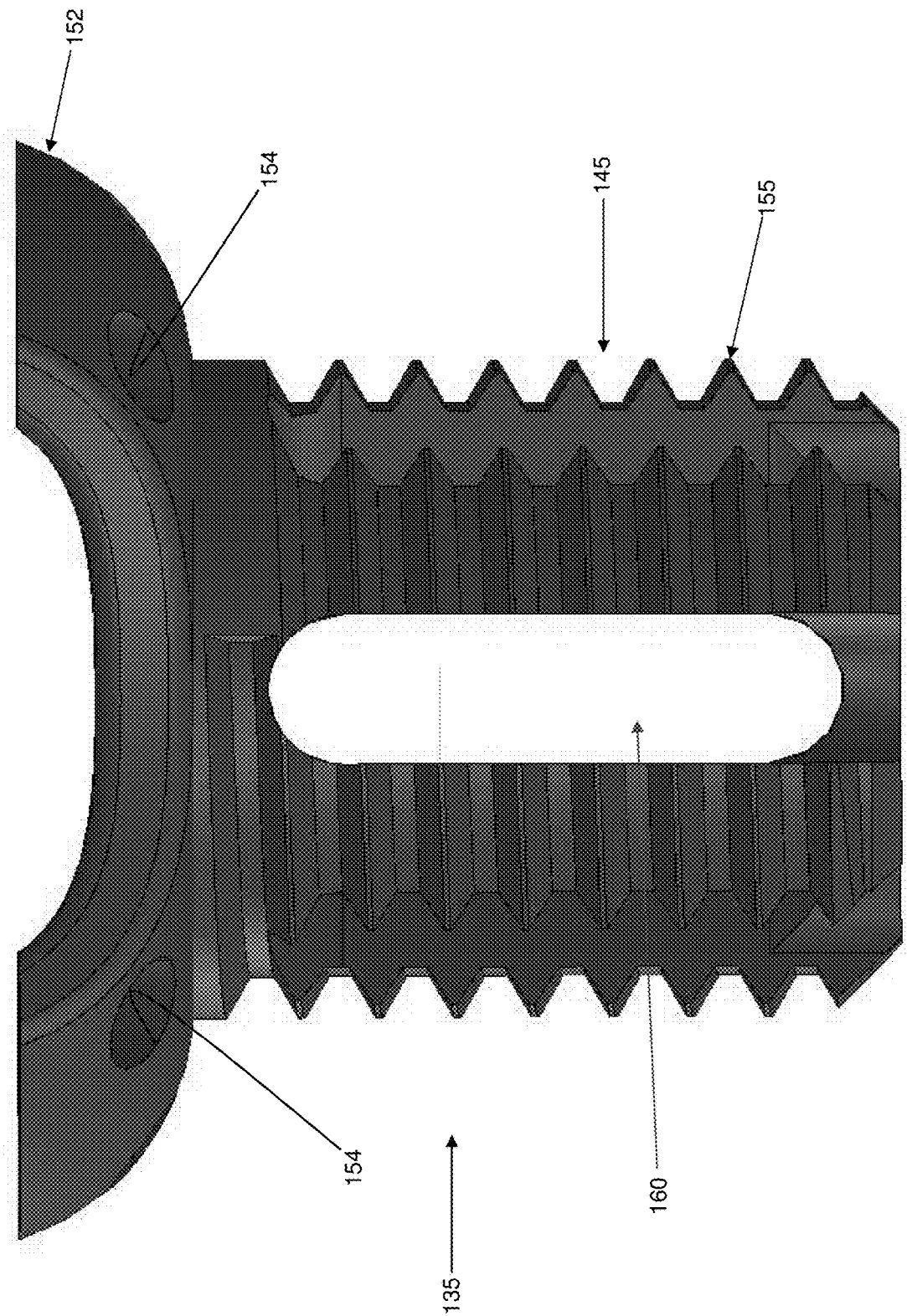
Figure 26:
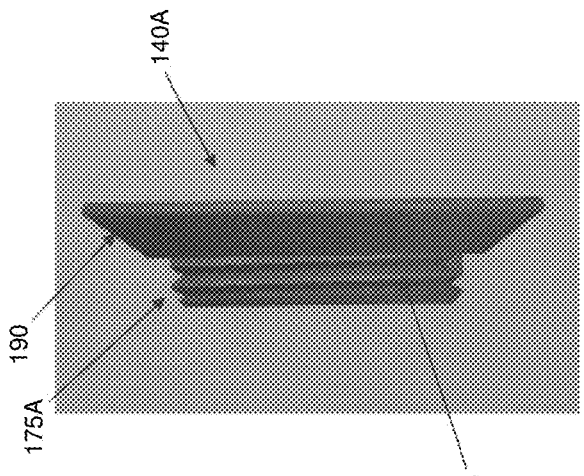
FIGS. 24-26 are schematic views showing another novel cap which may be mounted to the novel fusion barrel of FIGS. 15, 16A, 16B, 16C and 17-19.
Figure 24:
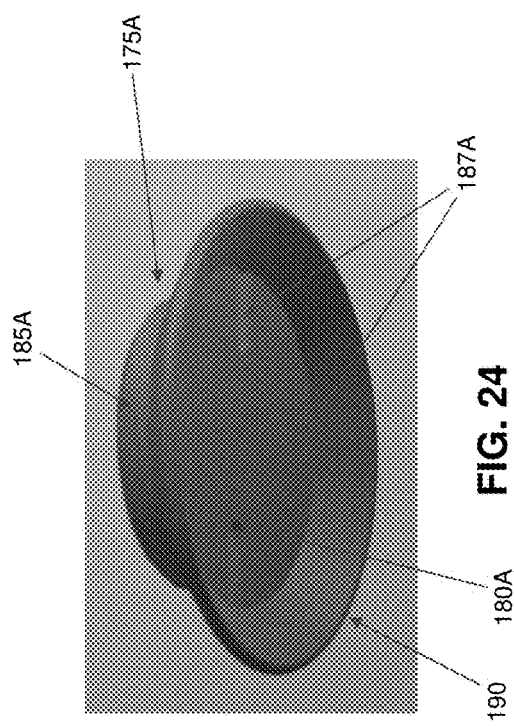
Figure 25:
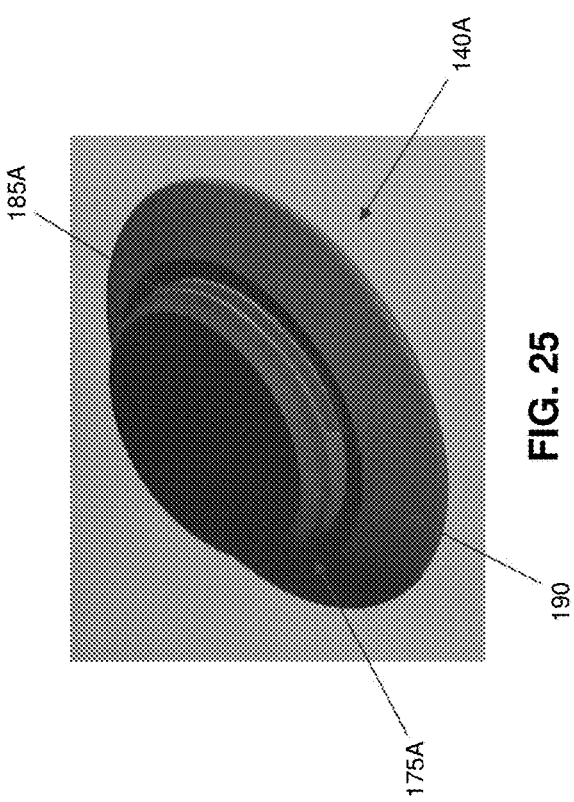
Figure 27:
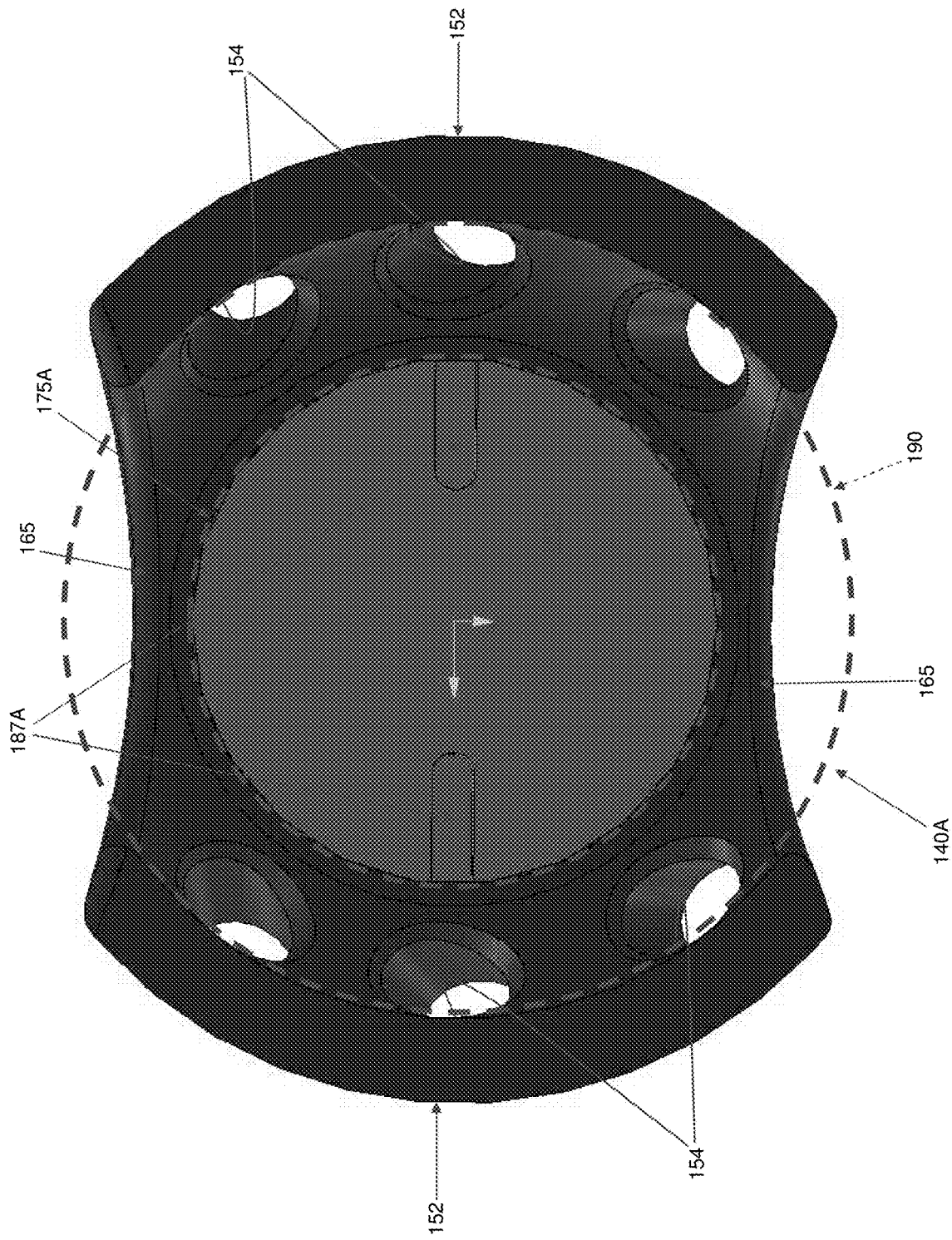
FIG. 27 is a schematic view showing the novel cap of FIGS. 24-26 mounted to the novel fusion barrel of FIGS. 15, 16A, 16B, 16C and 17-19.

More particularly, and looking now at FIGS. 17-19, fusion barrel 135 comprises a generally cylindrical, hollow body 145 terminating in a wall 150 at its distal end, and a radially-extending, generally spherical flange 152 at its proximal end. Wall 150 may comprise one or more openings 153 therein (FIG. 19), or wall 150 may be formed solid. Radially-extending, generally spherical flange 152 comprises a plurality of openings 154 for receiving a plurality of screws therein (not shown) which may be used to anchor fusion bullet 130 in bone. If desired, openings 154 may be threaded.

A first set of screw threads 155 is preferably provided on the outside of fusion barrel 135. This first set of screw threads 155 preferably extends along substantially the entire length of fusion barrel 135. One or more windows 160 (preferably in the form of flutes) are preferably provided on fusion barrel 135, with windows (flutes) 160 intersecting the first set of screw threads 155 and communicating with the interior of the fusion barrel. A seat 165 for receiving a driver (not shown) is preferably provided on the proximal end of fusion barrel 135. If desired, seat 165 may be formed by cutting away a portion of generally spherical flange 152 so as to provide a slot (or other seat) for receiving a corresponding driver (e.g., a driver comprising a flat sized to be received in seat 165). A second set of screw threads 170 is provided on the inside of fusion barrel 135. This second set of screw threads 170 preferably begins at the proximal end of fusion barrel 135 and extends distally into the interior of fusion barrel 135, at least part way along the length of the fusion barrel.

Solid cap 140 (FIGS. 20 and 21) preferably comprises a stem 175 extending distally from a substantially solid head 180. Stem 175 includes a set of screw threads 185 extending along its length which are sized to mate with screw threads 170 of fusion barrel 135 so as to releasably mount solid cap 140 to fusion barrel 135. Solid head 180 preferably comprises one or more depressions 187 (e.g., diametrically-opposed slots) formed on its proximal side for accepting a driver, whereby to allow a user to selectively rotate solid cap 140 and thereby secure the solid cap to fusion barrel 135 (or to selectively remove solid cap 140 from fusion barrel 135, e.g., by rotating solid cap 140 in the opposite direction). It should be appreciated that, if desired, solid cap 140 may be configured to snap into fusion barrel 135 rather than to screw into fusion barrel 135.

In use, fusion bullet 130 is mounted in bone in substantially the same manner as the aforementioned fusion bullet 30. More particularly, a bone hole (e.g., bore 90) is formed so that it straddles the two articular surfaces of a joint (or such that the bore straddles to portions of bone that are to be fused together). The bone hole is formed deep enough so that it passes through the hard cortical layer and penetrates into the softer cancellous layer. If desired, a counterbore (e.g., a counterbore 95) may also be drilled into the bone aligned with the bore. The counterbore is preferably of a depth such that generally spherical flange 152 will be recessed in the bone when fusion bullet 130 has been installed in the bone. Then fusion bullet 130 is installed in the bone hole straddling the joint line by inserting fusion barrel 135 into the bone hole and turning fusion barrel 135 using a driver (not shown). One or more fasteners (e.g., screws, pins, sutures, etc.) are then passed through openings 154 of radially-extending, generally spherical flange 152 and into the bone on either side of the joint line, whereby to secure radially-extending, generally spherical flange 152 (and hence fusion bullet 130) to the bones. It will be appreciated that, at this point, fusion bullet 130 is mounted into the bones, straddling the joint line, in its "final" position. Bone graft material and/or bone growth promoting material can then be inserted into hollow body 145 of fusion barrel 135 so that the bone graft material communicates with the surrounding cancellous bone (e.g., via windows/flutes 160 and opening(s) 153). Then solid cap 140 can be installed (i.e., by mating screw threads 185 of solid cap 140 with corresponding screw threads 170 of fusion barrel 135), whereby to seal hollow body 145 and complete the procedure.

It should be appreciated that fusion bullet 130 may be made out of any material suitable for implantation into the body (e.g., metal, PEEK, PEEK HA, etc.). Where fusion bullet 130 comprises metal or another suitable material, fusion bullet 130 may be configured to be self-tapping so as to facilitate easy installation into bone. Where fusion bullet 130 comprises plastic (e.g., PEEK), the bone hole may be tapped, or screw threads 155 on the outer surface of fusion barrel 135 may be replaced by flexible ribs.

And it should be appreciated that fusion bullet 130 may be provided in various sizes for use in different applications (e.g., for use in the wrist, hand, foot, ankle, etc.) without departing from the scope of the present invention.

It should also be appreciated that, if desired, solid cap 140 can be configured to cover openings 154 of radially-extending, generally spherical flange 152 so as to prevent the fasteners (e.g., screws) 100 disposed in openings 154 of generally spherical flange 152 from "backing out" of openings 154. By way of example but not limitation, and looking now at FIGS. 24-27, there is shown an alternative solid cap 140A.

Solid cap 140A preferably comprises a stem 175A extending distally from a substantially solid head 180A. Stem 175A includes a set of screw threads 185A extending along its length which are sized to mate with screw threads 170 of fusion barrel 135. Solid head 180A comprises one or more depressions 187A formed in its proximal side for accepting a driver, whereby to allow a user to selectively rotate solid cap 140A and thereby secure solid cap 140A to fusion barrel 135 (or to selectively remove solid cap 140A from fusion barrel 135, e.g., by rotating solid cap 140A in the opposite direction). It should be appreciated that, if desired, solid cap 140A may be configured to snap into fusion barrel 135 rather than to screw into fusion barrel 135.

Solid cap 140A also comprises a radially-extending flange 190. Radially-extending flange 190 is preferably configured so as to cover openings 154 of radially-extending, generally spherical flange 152 when solid cap 140A is mated to fusion bullet 130. See FIG. 27.

As a result of this construction, when fusion bullet 130 is installed in bone and secured in place, with one or more screws passing through openings 154 and with solid cap 140A secured to fusion barrel 135, radially-extending flange 190 of solid cap 140A covers openings 154 of fusion barrel 135, whereby to prevent "backing out" of the screws disposed in openings 154.

Additional Applications

While the present invention has generally been discussed in the context of fusing a joint between two articulating bones, it should also be appreciated that the present invention may be used to fuse substantially any two (or more) adjacent bones or portions of adjacent bone, including portions of bone which do not natively articulate (e.g., portions of bone separated by a fracture line).

Modifications

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for stabilizing a first portion of bone relative to a second portion of bone, said method comprising:
    providing an apparatus comprising:
        a fusion barrel for disposition between the first portion of bone and the second portion of bone, said fusion barrel comprising:
            a tubular body having a distal end, a proximal end, and a cavity formed in said tubular body, said cavity comprising a distal end and a proximal end;
            at least one opening formed in said tubular body in fluid communication with said cavity of said tubular body; and
            a radially-extending flange formed integral with said tubular body such that said radially-extending flange and said tubular body together comprise a single, indivisible unit, said radially-extending flange extending radially of said proximal end of said tubular body such that said radially-extending flange extends around at least a portion of said proximal end of said tubular body;
            wherein said radially-extending flange comprises a plurality of openings passing completely through said radially-extending flange; and
        a cap configured to be releasably mounted to said proximal end of said tubular body so as to seal said proximal end of said cavity;
    forming a hole in the joint space between the first portion of bone and the second portion of bone such that the hole extends parallel to the joint space and into the first portion of bone and the second portion of bone;

inserting bone graft material and/or bone growth promoting material into said cavity;

mounting said cap to said proximal end of said tubular body so as to seal said proximal end of said cavity without covering said plurality of openings of said radially-extending flange;

inserting said tubular body of said fusion barrel into the hole; and after said tubular body of said fusion barrel has been inserted into the hole, passing at least one fastener through one of said plurality of openings in said radially-extending flange such that said at least one fastener passes into at least one of the first portion of bone and the second portion of bone.

2. The method according to claim 1 wherein screw threads are formed at said proximal end of said cavity, wherein said cap comprises a distally-extending stem having screw threads thereon, and further wherein said screw threads formed on said distally-extending stem of said cap are configured to mate with said screw threads formed at said proximal end of said cavity.

3. The method according to claim 1 wherein said plurality of openings formed in said radially-extending flange are disposed at an angle relative to a longitudinal axis of said cavity.

4. The method according to claim 3 wherein said plurality of openings formed in said radially-extending flange are threaded.

5. The method according to claim 1 wherein said radially-extending flange extends radially on two diametrically opposed sides of said tubular body of said fusion barrel, and further wherein said radially-extending flange is recessed on another two sides of said tubular body.

6. The method according to claim 1 wherein said tubular body comprises an outer surface, and further wherein said outer surface comprises a screw thread for screwing said fusion barrel into the hole formed in the bone.

7. The method according to claim 6 wherein said outer surface comprises a plurality of flexible ribs.

8. The method according to claim 1 wherein said tubular body comprises a plurality of regularly-spaced openings in fluid communication with said cavity.

9. The method according to claim 1 wherein said plurality of openings in said radially-extending flange are threaded.

10. The method according to claim 1 wherein at least two fasteners are passed through two of said plurality of openings in said radially-extending flange, such that at least one of said at least two fasteners engages the first portion of bone and at least one of said at least two fasteners engages the second portion of bone.

11. The method according to claim 1 wherein said cap is solid.

12. The method according to claim 1 wherein said cap comprises at least one opening for receiving a driver.

13. The method according to claim 12 wherein said at least one opening comprises a pair of diametrically-opposed recesses.

14. The method according to claim 1 wherein at least a portion of said radially-extending flange is recessed so as to provide a seat for receiving a driver, such that said driver may be used to turn said fusion barrel.

15. The method according to claim 1 wherein the step of forming a hole in the joint space between the first portion of bone and the second portion of bone such that the hole extends parallel to the joint space and into the first portion of bone and the second portion of bone further comprises the step of forming a counterbore aligned with the hole formed in the joint space, wherein the counterbore extends into the first portion of bone and the second portion of bone, whereby to receive said radially-extending flange formed integral with said tubular body, such that said radially-extending flange is recessed in the bone when said tubular body is inserted into the hole in the joint space.

* * * * *